(12) United States Patent
O'Connell et al.

(10) Patent No.: US 9,757,774 B2
(45) Date of Patent: Sep. 12, 2017

(54) PASSIVE SAMPLING DEVICES

(71) Applicant: MyExposome, Inc., Philadelphia, PA (US)

(72) Inventors: Steven O'Connell, Corvallis, OR (US); Kim Anderson, Corvallis, OR (US)

(73) Assignee: MyExposome, Inc., Philadelphia, PA (US)

(*) Notice: Subject to any disclaimer, the term of this patent is extended or adjusted under 35 U.S.C. 154(b) by 118 days.

(21) Appl. No.: 14/597,817

(22) Filed: Jan. 15, 2015

(65) Prior Publication Data

US 2016/0209298 A1   Jul. 21, 2016

(51) Int. Cl.
| | | |
|---|---|---|
| *G01N 33/24* | (2006.01) | |
| *G01N 1/22* | (2006.01) | |
| *B08B 3/12* | (2006.01) | |
| *B08B 7/00* | (2006.01) | |
| *G01N 30/72* | (2006.01) | |
| *G01N 30/88* | (2006.01) | |

(52) U.S. Cl.
CPC ............. *B08B 3/12* (2013.01); *B08B 7/0071* (2013.01); *G01N 1/2273* (2013.01); *G01N 30/72* (2013.01); *G01N 33/24* (2013.01); *G01N 2001/2276* (2013.01); *G01N 2030/8813* (2013.01)

(58) Field of Classification Search
CPC .......... B08B 3/08; B08B 3/12; B08B 7/0071; G01N 1/2273; G01N 2001/2276; G01N 30/72; G01N 33/24; G01N 2030/8813
USPC ....... 436/104, 139, 161, 173, 174, 177, 178, 436/181; 422/69, 70, 83, 88, 89, 527, 422/535
See application file for complete search history.

(56) References Cited

U.S. PATENT DOCUMENTS

| | | | | |
|---|---|---|---|---|
| 3,985,017 A | * | 10/1976 | Goldsmith | ........... G01N 1/2273 422/83 |
| 4,040,805 A | | 8/1977 | Nelms et al. | |
| 4,231,249 A | * | 11/1980 | Zuckerman | ........ G01N 33/0062 340/632 |
| 4,597,942 A | * | 7/1986 | Meathrel | .............. G01N 31/223 422/408 |
| 6,132,765 A | | 10/2000 | DiCosmo | |
| 7,559,980 B2 | * | 7/2009 | Guild | .................... G01N 1/2273 422/88 |
| 2002/0148355 A1 | | 10/2002 | Smith et al. | |
| 2006/0045899 A1 | | 3/2006 | Sarangapani | |
| 2006/0086665 A1 | * | 4/2006 | Wenzel | .............. B01D 11/0415 210/644 |

(Continued)

OTHER PUBLICATIONS

Kile et al. Environmental Research, vol. 147, Mar. 3, 2016, pp. 365-372.*

(Continued)

*Primary Examiner* — Maureen Wallenhorst
(74) *Attorney, Agent, or Firm* — Fish & Richardson P.C.

(57) ABSTRACT

A method includes receiving a wearable monitoring device worn by a user and information indicative of an amount of time the wearable monitoring device was exposed to an environment; extracting one or more compounds from the wearable monitoring device; analyzing the extracted compounds; and, based on the analysis of the extracted compounds and the information indicative of the amount of time, determining information indicative of the user's exposure to the compounds in the environment.

39 Claims, 15 Drawing Sheets

(56) References Cited

U.S. PATENT DOCUMENTS

| | | | |
|---|---|---|---|
| 2006/0141466 A1* | 6/2006 | Pinet | G01N 21/23 435/6.11 |
| 2010/0078856 A1 | 4/2010 | Cueto | |
| 2013/0042378 A1 | 2/2013 | Wu | |
| 2014/0069184 A1* | 3/2014 | McAlary | E21B 49/081 73/152.28 |
| 2015/0189930 A1 | 7/2015 | Roth | |
| 2017/0023509 A1 | 1/2017 | Kim | |
| 2017/0043381 A1 | 2/2017 | O'Connell et al. | |

OTHER PUBLICATIONS

Barrington et al. European Journal of Nuclear Medicine, vol. 26, No. 7, Jul. 1999, pp. 686-692.*

Allan et al., "Should silicone prostheses be considered for specimen banking? A pilot study into their use for human biomonitoring", *Enviornment International*, 59 (2013) 462-468.

O'Connell et al., "Silicone Wristbands as Personal Passive Samplers", *Environ. Sci. Technol.*, 2014, 48, 3327-3335.

Amazon.com, "deet bracelet" search results, <URL: http://www.amazon.com/s/?ie=UTF8&keywords=deet+bracelet&tag=googhydr-20&index=aps&hvadid=34592626248&hvpos=1t1&hvexid=&hvnetw=g&hvrand=15036622953483001392&hvpone=&hvptwo=&hvqmt=b&hvdev=c&ref=pd_sl_9t0zw09zhg_b>, retrieved from the Internet on Feb. 28, 2017. 6 pages.

Amazon.com. "trashbags scented,"search results, <URL: https://www.amazon.com/s/ref=nb_sb_noss?url=search-alias%3Daps&field-keywords=TRASHBAGS+SCENTED&rh=i%3Aaps%2Ck%3ATRASHBAGS+SCENTED>. retrieved from the Internet on Feb. 28, 2017, 5 pages.

O'Connell. "Silicone Wristbands as Personal Passive Samplers." 28 slides. NOHC Talk, Oct. 13, 2014.

Abstract for Kau, Ng Chun. HK 1079037, Mar. 24, 2006.

[No Author Listed] "Taking Good Care of Your Silicone Wristbands", Interesting Articles.com. 2012-2013, http://www.interestingarticles.com/business-advertising/taking-good-care-of-your-silicone-wristbands-12151.html, dated Mar. 28, 2017, 2 pages.

Donald et al. "Silicone wristbands detect individuals' pesticide exposures in West Africa," *Royal Society Open Science.*, 3(8):160433, pp. 1-13, Aug. 2016.

O'Connell et al. "Improvements in pollutant monitoring: Optimizing silicone for co-deployment with polyethylene passive sampling devices," *Environmental Pollution.*, vol. 193:71-78, Jul. 7, 2014.

* cited by examiner

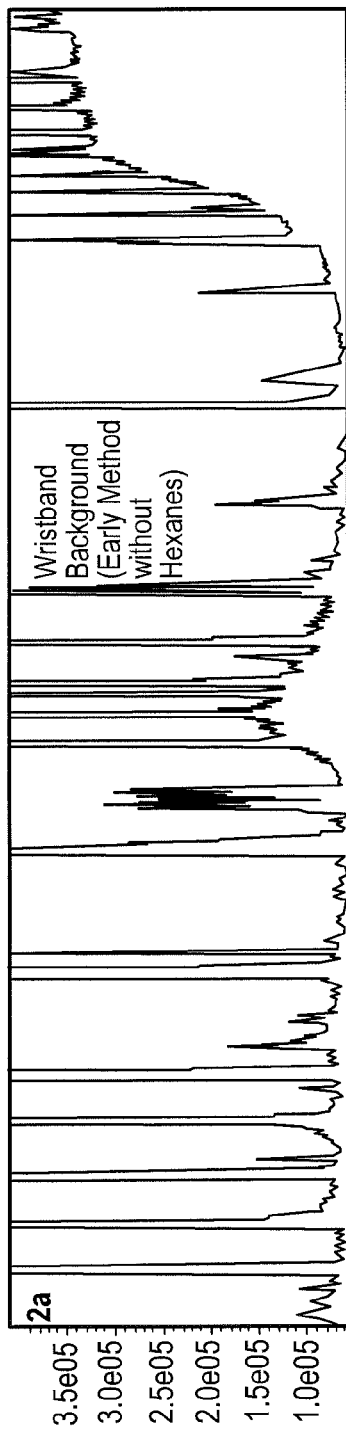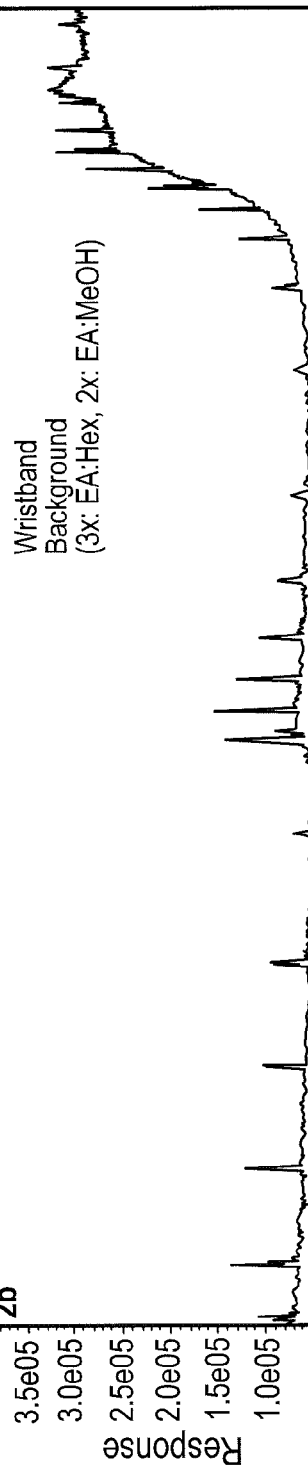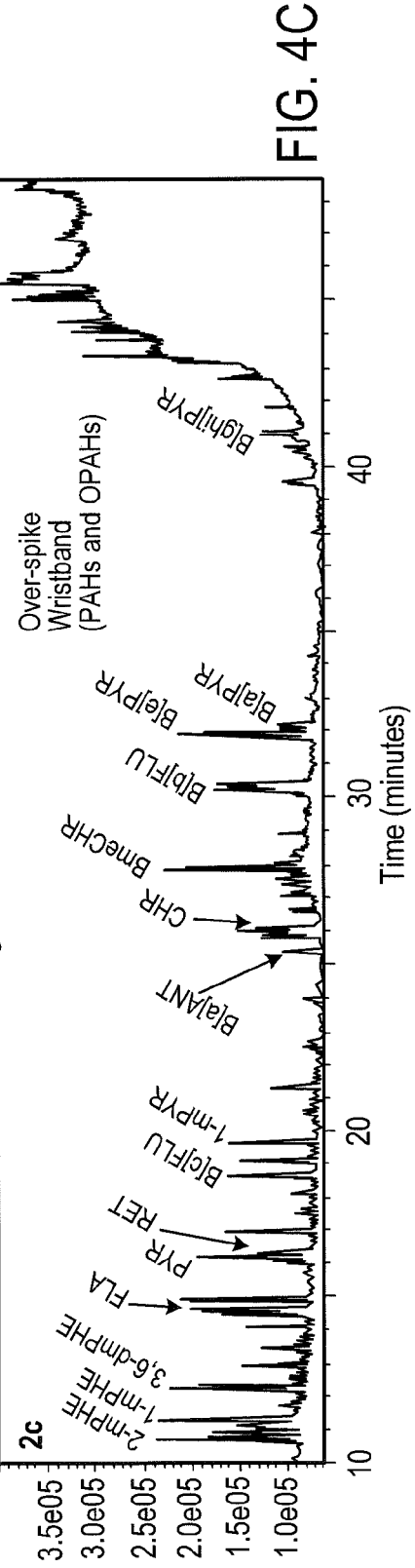

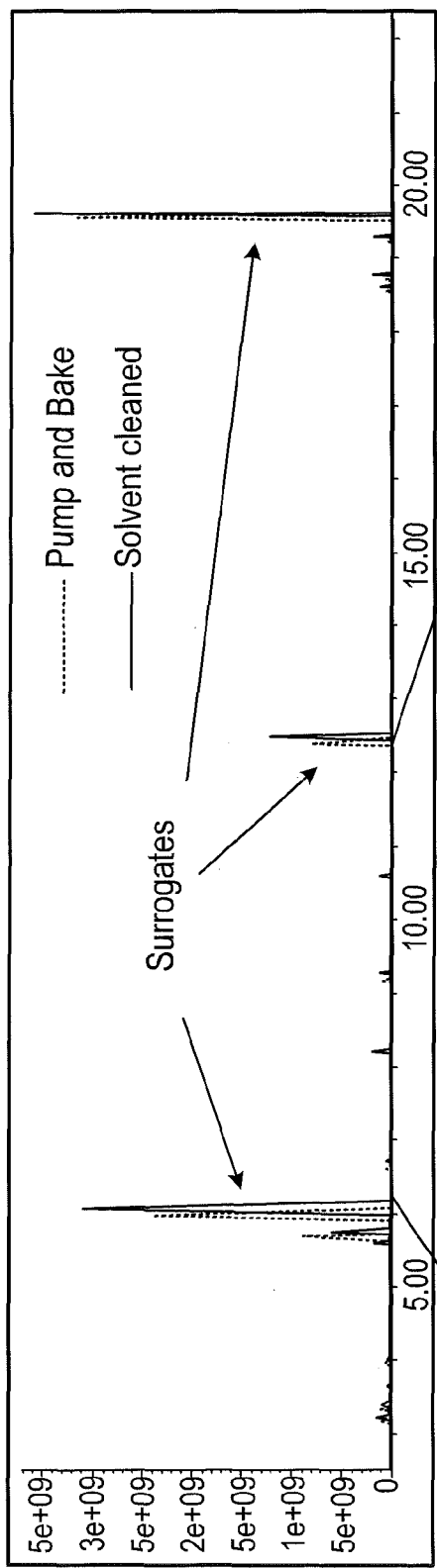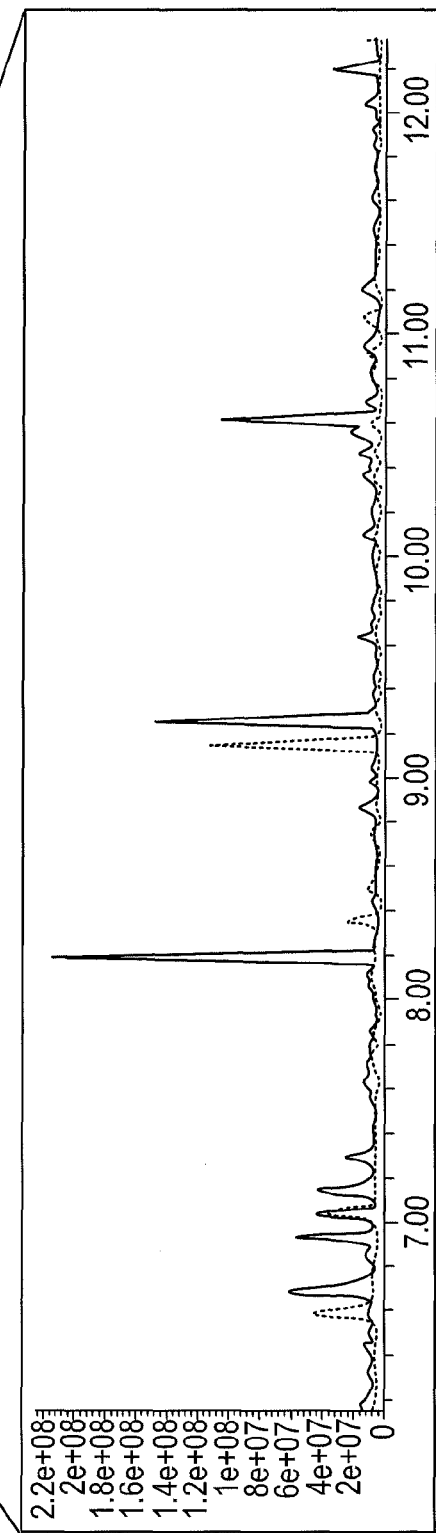
FIG. 6A
FIG. 6B

PASSIVE SAMPLING DEVICES

STATEMENT AS TO FEDERALLY SPONSORED RESEARCH

This invention was made with government support under grant number P42 ES016465, P30 ES000210, R21 ES020120, and T32 ES007060-32 awarded by The National Institutes of Health (NIH). The government has certain rights in the invention.

BACKGROUND

People can be exposed to a complex mixture of natural and man-made compounds through work-related exposure or interactions with the ambient environment. A person can be exposed to compounds in the environment through pathways such as dermal, oral, or inhalation pathways. Sampling of compounds from the environment can be used to measure a person's exposure to those compounds.

SUMMARY

In an aspect, a method includes receiving a wearable monitoring device worn by a user and information indicative of an amount of time the wearable monitoring device was exposed to an environment; extracting one or more compounds from the wearable monitoring device; analyzing the extracted compounds; and, based on the analysis of the extracted compounds and the information indicative of the amount of time, determining information indicative of the user's exposure to the compounds in the environment.

Embodiments can include one or more of the following features.

The method includes purifying the wearable monitoring device. Purifying the wearable monitoring device includes cleaning the wearable monitoring device with a solvent. Purifying the wearable monitoring device includes heat treating the wearable monitoring device. The method includes providing the wearable monitoring device to the user.

The method includes infusing a reference compound into the wearable monitoring device.

Providing a purified wearable monitoring device to a user includes providing the purified wearable monitoring device in an airtight container. The method includes receiving, from the user, the wearable monitoring device in the airtight container. The airtight container includes a re-sealable bag.

The method includes providing pre-paid return packaging to the user, and wherein receiving the wearable monitoring device from the user comprises receiving the wearable monitoring device in the pre-paid return packaging.

Extracting one or more compounds from the wearable monitoring device includes extracting the compounds using a solvent extraction process. The method includes extracting the compounds into a solvent that is compatible with gas chromatography and liquid chromatography. The method includes extracting the compounds into ethyl acetate.

Extracting one or more compounds from the wearable monitoring device includes thermally desorbing the compounds from the wearable monitoring device.

Extracting one or more compounds from the wearable monitoring device includes extracting one or more of polycyclic aromatic hydrocarbon compounds, compounds from consumer products, pesticides, phthalates, industrial compounds, or volatile organic acids.

Analyzing the extracted compounds includes determining one or more of an identity of each of the compounds or an amount of each of the compounds present in the wearable monitoring device.

Determining information indicative of the user's exposure to the compounds in the environment includes determining a time-weighted average of the user's exposure to each of the compounds.

The method includes archiving one or more of (i) the extracted compounds or (ii) all or a portion of the wearable monitoring device.

The wearable monitoring device includes silicone.

The wearable monitoring device includes a wristband.

In an aspect, an assembly includes a purified wearable monitoring device formed of silicone; and an airtight package for storing the wearable monitoring device.

Embodiments can include one or more of the following features.

The wearable monitoring device includes a wristband.

The wearable monitoring device includes a lapel pin.

When the purified wearable monitoring device is exposed to a subsequent purification, the weight of the purified wearable monitoring device is reduced by less than about 0.2%.

The airtight package includes a re-sealable bag.

The purified wearable monitoring device includes a known amount of a reference compound.

The assembly includes instructions enabling a user to return the wearable monitoring device to an analysis facility.

In an aspect, a method includes removing a purified wearable monitoring device from an airtight package; exposing the wearable monitoring device to an environment; tracking an amount of time for which the wearable monitoring device is exposed to the environment; and sealing the wearable monitoring device in an airtight package for transport to an analysis facility for analysis of compounds sequestered by the wearable monitoring device during exposure of the wearable monitoring device to the environment.

Embodiments can include one or more of the following features.

The wearable monitoring device includes a wristband.

Exposing the wearable monitoring device to an environment includes wearing the wearable monitoring device in the environment.

The method includes intermittently exposing the wearable monitoring device to the environment; and tracking a total amount of time for which the wearable monitoring device is exposed to the environment.

The method includes including, in or with the airtight package, an indication of the amount of time for which the wearable monitoring device was exposed to the environment.

In an aspect, a method includes purifying a silicone wearable monitoring device, including exposing the wearable monitoring device to one or more of a solvent treatment or a heat treatment to remove target compounds from the wearable monitoring device, wherein, when the purified wearable monitoring device is exposed to a subsequent solvent treatment or heat treatment, a weight of the purified wearable monitoring device is reduced by less than about 0.2%.

Embodiments can include one or more of the following features.

Exposing the wearable monitoring device to a solvent treatment includes cleaning the wearable monitoring device with one or more of methanol, hexane, or ethyl acetate.

Exposing the wearable monitoring device to a solvent treatment includes agitating or sonicating the wearable monitoring device in a solvent.

Exposing the wearable monitoring device to a heat treatment includes heat treating the wearable monitoring device at a pressure of less than about 550 mm Hg.

Exposing the wearable monitoring device to a heat treatment includes heating the wearable monitoring device to a temperature of at least about 250° C.

Purifying the wearable monitoring device causes the weight of the wearable monitoring device to be reduced by greater than about 0.2%.

The method includes providing the purified wearable monitoring device to be deployed by a user. The method includes receiving the wearable monitoring device following deployment by the user; and analyzing the purified wearable monitoring device for the target compounds.

The method includes infusing a reference compound into the purified wearable monitoring device.

The method includes sealing the purified wearable monitoring device in an airtight container.

The passive sampling devices described herein can have one or more of the following advantages. The passive sampling devices can be easy to use, lightweight, and unobtrusive, which can encourage a user to use the passive sampling device as directed. The passive sampling devices can be conditioned prior to use to remove background impurities, thus allowing the compounds sequestered by the passive sampling devices during deployment to be more readily detected. The passive sampling devices are capable of sequestering a wide range of compounds having a variety of properties, and thus analysis of these devices can present an informative depiction of the compounds to which users of the devices were exposed.

Other features and advantages are apparent from the following description and from the claims.

BRIEF DESCRIPTION OF DRAWINGS

FIGS. 4A-4C are total ion chromatograms of wristband extracts.

FIGS. 6A and 6B are chromatograms of extracts from wristbands conditioned with different processes.

DETAILED DESCRIPTION

We describe here a passive sampling device, such as a wristband, that can be used to monitor a person's exposure to various compounds in his environment. Prior to use, the passive sampling device is cleaned to remove impurities. When the passive sampling device is placed in the environment, compounds from the environment diffuse into the material of the passive sampling device, thus capturing a representation of the compounds to which the person was exposed in the environment. After exposure to the environment, the compounds are extracted from the passive sampling device and the extract is analyzed to identify the compounds to which the person was exposed. Based on the amount of time the passive sampling device was deployed in the environment, a time-weighted average exposure to each compound can be determined. The passive sampling device can thus be used as a personal monitoring device that can provide a person with information about his exposure to various compounds in his daily life, while he is at work, or in other situations.

Figure 1:
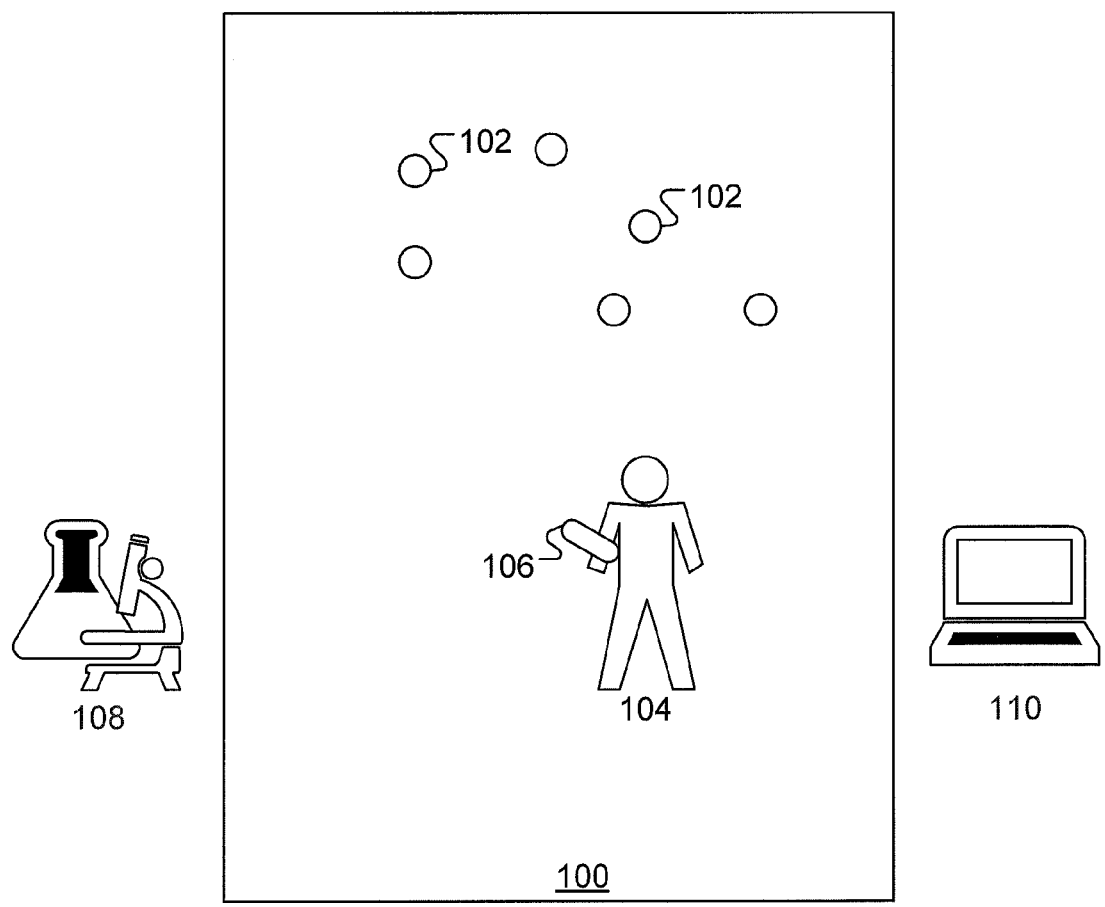
FIG. 1 is a diagram of a passive sampling device deployed in an environment.

Referring to FIG. 1, an environment 100 often includes a wide range of compounds 102, such as natural compounds or man-made compounds, to which a person 104 in the environment 100 is exposed. Person 104 can use a passive sampling device 106 to monitor his exposure to various compounds, such as environmental contaminants. For instance, person 104 can wear or otherwise use the passive sampling device 106 for a period of time in the environment 100. During use, passive sampling device 106 sequesters compounds in environment 100. Subsequent chemical analysis of passive sampling device 106 can provide a qualitative or quantitative indication of one or more compounds to which passive sampling device 106 (and hence person 104) was exposed. For instance, passive sampling device 106 can act as a dosimeter that provides a time-weighted average exposure of person 104 to each of various compounds in his environment 100.

In general, a passive sampling device provided herein is a monitoring device that is capable of sequestering one or more types of compounds 102 from an environment. In some cases, sequestering a compound can include capturing a compound within a material of the passive sampling device by absorption, adsorption, or another mechanism. For instance, compounds 102 can passively diffuse into passive sampling device 106, e.g., from air or water.

Passive sampling device 106 can be chemically analyzed by an analysis element 110 subsequent to its use in the environment to identify compounds 102 sequestered by passive sampling device 106. Quantitative chemical analysis of passive sampling device 106 can provide a quantitative measure of the exposure of passive sampling device 106 (and hence exposure of the person 104) to compounds 102 sequestered by passive sampling device 106. For instance, a time-weighted average of the person's exposure to each of sequestered compounds 102 can be determined based on the amount of each compound 102 sequestered by passive sampling device 106 and the amount of time for which passive sampling device 106 was used. In some examples, passive sampling device 106 can be cleaned by a cleaning element 108 prior to exposure to the environment to reduce impurities present in the passive sampling device.

Passive sampling device 106 can take a variety of forms. For instance, a passive sampling device provided herein can be a personal accessory, such as jewelry (e.g., a wristband or bracelet, a lapel pin, a necklace, a necklace or bracelet charm, or other jewelry), a watch band (e.g., a band for a smart watch or another type of wrist-worn device), a dog tag holder or cover, a helmet strap, a holder for an employee card or access badge, or another type of personal accessory. In some cases, a passive sampling device provided herein can be shaped to be used with an electronic device; for instance, a passive sampling device can be a case for a mobile phone, tablet, camera, accelerometer, audio/visual transmitter, lens, measuring device; a sound dampening cushion; or other electronic device or instrument. In some cases, a passive sampling device provided herein can be a small membrane that can be secured onto a personal device or into a chamber of a personal device, such as a personal electronic device. In some cases, a passive sampling device provided herein can be affixed to an item worn or used by a person, such as a harness, weapon, helmet, piece of personal protective equipment, or other item. In some cases, a passive sampling device provided herein can be affixed to a mechanical device, such as a multirotor or fixed-wing unmanned aerial vehicle (drone). In some cases, a passive sampling device provided herein can be a small article, such as an article to be hung on a wall or doorknob, an adhesive article to be stuck to an item in a room, or another type of small article. In some cases, a passive sampling device provided herein can be designed to be deployed on or with an animal, e.g., affixed to a companion or rural animal harness or leash or affixed to the animal itself as an ear tag.

In some cases, a passive sampling device provided herein can be individually tagged or otherwise identified, e.g., by embossing, debossing, or printing; by including a feature that is scannable or barcode readable; by embedding a robust radio frequency identification (RFID) sensor or tag therein; or in another way. In some cases, a passive sampling device provided herein can be stable prior to or subsequent to deployment, e.g., for several months, a year, or several years. In some cases, a passive sampling device provided herein can be stable under a variety of conditions, such as sunny conditions, high temperatures, low temperatures, or other conditions. In some cases, a passive sampling device provided herein can be robust against standard activities a wearer might undertake, such as standard conditions at work, home, or school; swimming; showering; or other activities. Passive sampling devices provided herein can be used in a wide variety of situations, such as government or military applications, agricultural usage, unions or other occupational usage, or general public commercial occupations.

Figure 2A:
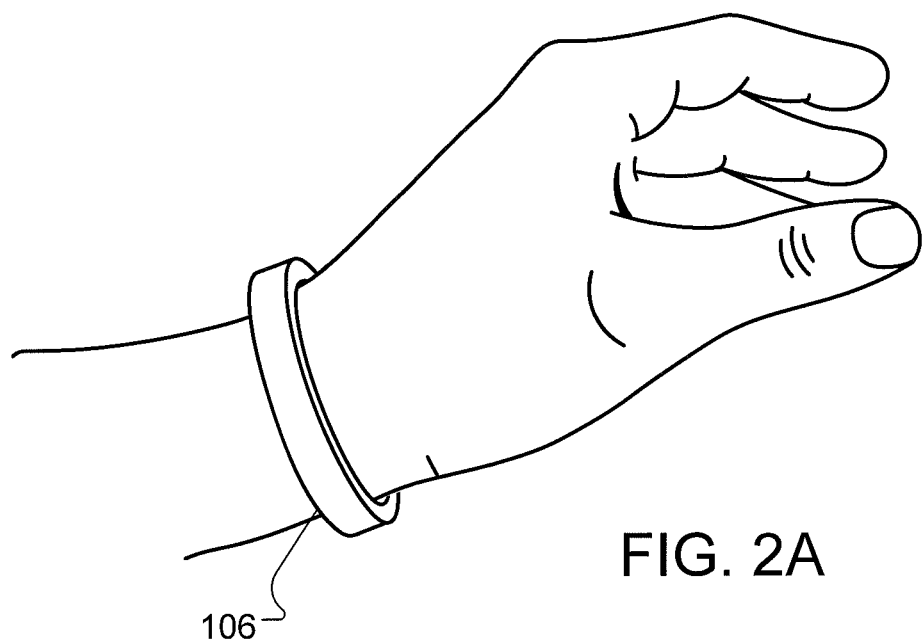
FIGS. 2A and 2B are photographs of a wristband sealed in an airtight container.
Figure 2B:
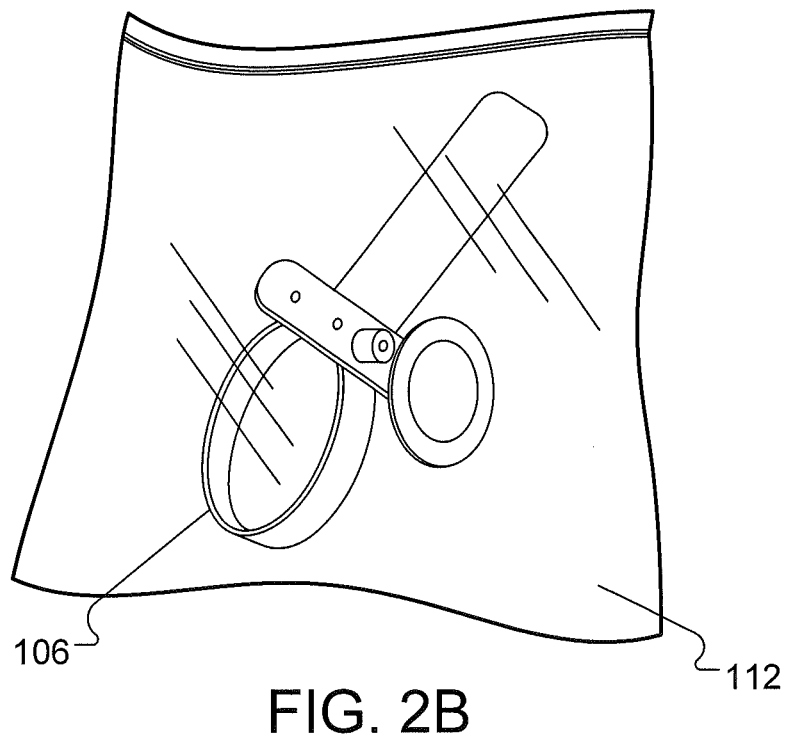

Referring to FIGS. 2A and 2B, in some cases, passive sampling device 106 is a silicone wristband. The wristband 106 can be stored in an airtight container 112, such as a bag or box. In the example of FIGS. 2A and 2B, the passive sampling device 106 is a silicone wristband and the airtight container 112 is a re-sealable polytetrafluoroethylene bag. In some examples, passive sampling device 106 can be stored in airtight container 112 after cleaning and prior to use in environment 100 so that passive sampling device 106 does not begin to sequester compounds until person 104 intends to use passive sampling device 106. In some examples, passive sampling device 106 can be stored in airtight container 112 after exposure to the environment 100 so that passive sampling device 106 does not continue to sequester compounds after person 104 has finished using passive sampling device 106. In some examples, passive sampling device 106 can be stored in same container 112 both prior to and subsequent to exposure to the environment 100. Airtight container 112 can include a space to indicate an identifier of person 104, such as the person's name and/or an identification number. Airtight container 112 can include a space to indicate exposure conditions, such as exposure date(s), amount of time for which the passive sampling device 106 was worn or used in an environment, location or environment information, or other information about exposure conditions.

Figure 3:
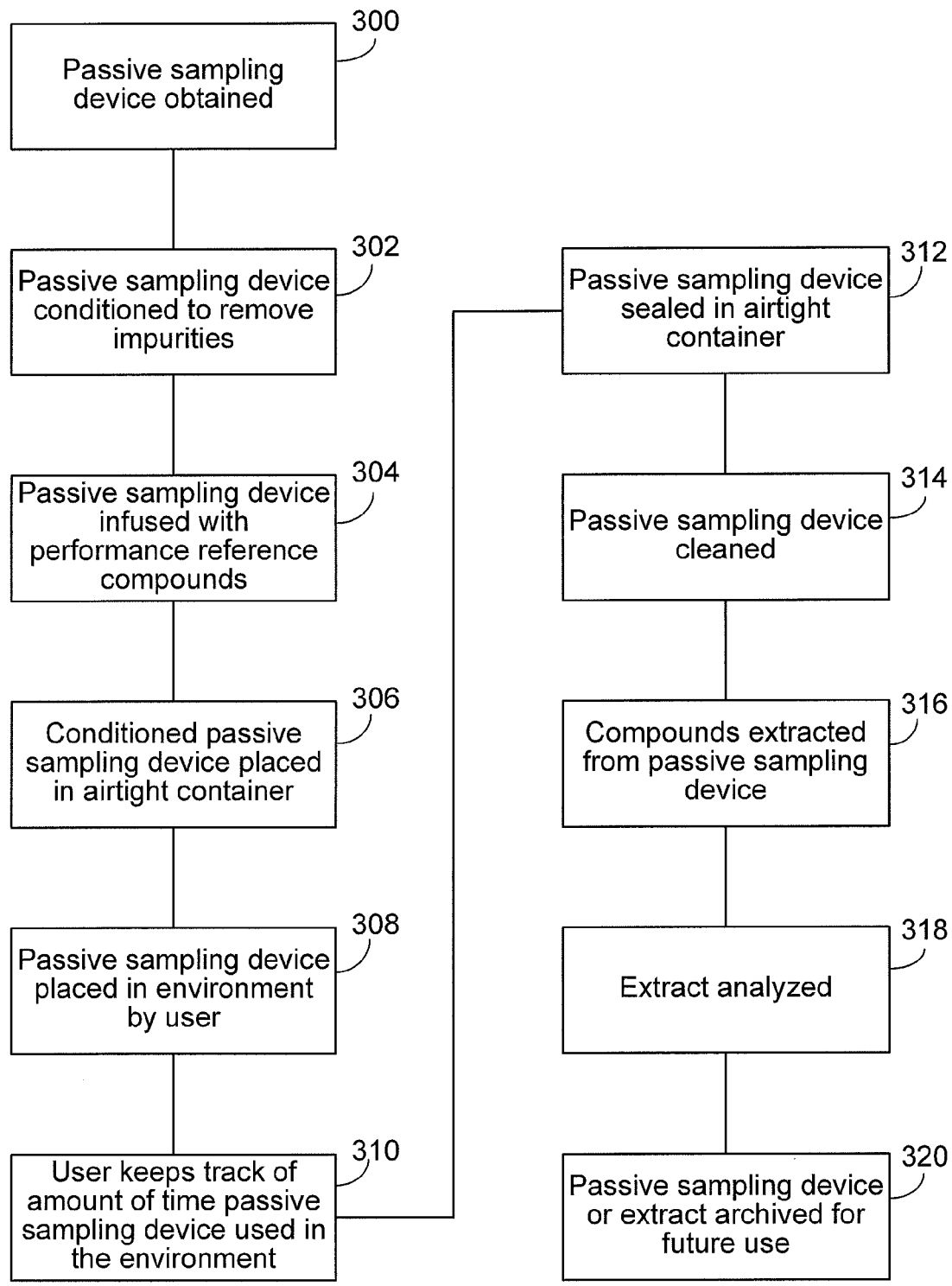
FIG. 3 is a flowchart.

FIG. 3 shows a general process for preparing, using, and analyzing a passive sampling device. A passive sampling device, such as a wristband, is obtained from a commercial supplier or fabricated (300). The passive sampling device is made of a material that is capable of sequestering various types of compounds, such as an absorbent material that is porous or permeable and can adsorb or absorb the desired types of compounds. For instance, the passive sampling device can be made of a polymer, such as silicone, low density polyethylene, or another material.

In some examples, the passive sampling device can be capable of sequestering both hydrophobic and hydrophilic compounds, such as compounds having a wide range of partition coefficients. For instance, the passive sampling device can be capable of sequestering compounds having a wide range of octanol/water partition coefficient ($K_{ow}$) values (e.g., compounds with log $K_{ow}$ values ranging from less than zero to at least about 10). Example compounds that can be sequestered by a passive sampling device can include polycyclic aromatic hydrocarbon (PAH) or oxygenated PAH (OPAH) compounds, compounds from consumer products (e.g., fragrances, nicotine, caffeine, or other consumer product compounds), pesticides, phthalates, industrial compounds (e.g., flame retardants, pain components, disinfectants, or other industrial compounds), volatile organic chemicals, or other types of compounds.

Prior to use, the passive sampling device is conditioned to remove impurities from the device (302). The conditioning treatment helps to ensure that any compounds detected during subsequent analysis of the passive sampling device are compounds that were sequestered by the passive sampling device during a user's intentional use of the device and not compounds that were initially present in the passive sampling device. Conditioning processes can include one or more of heating, soaking in solvents, such as organic solvents, or infusion of performance reference compounds. Conditioning processes can take place at atmospheric pressure, reduced pressure, or increased pressure, as seen with accelerated solvent extraction techniques.

In some examples, measurable amounts of impurities are removed from the passive sampling device during conditioning. For instance, the conditioning treatment can result in a measurable weight reduction of the passive sampling device due to removal of the impurities, e.g., a weight reduction of at least 0.2%, at least 1%, at least 2%, or at least 3%, e.g., a weight reduction of between about 0.2% and about 3.1%. In some examples, when the conditioning treatment is repeated (e.g., such that a conditioned passive sampling device is subjected to a second conditioning treatment), a smaller weight reduction occurs, e.g., a weight reduction of less than about 0.2% or less than about 0.1%.

In some examples, a goal of the conditioning treatment is to remove from the passive sampling device any compounds for which the passive sampling device will be screened following deployment (which we sometimes refer to as target compounds). For instance, the conditioning treatment can reduce the presence of some or all of the target compounds in the wristband to a level that is not detectable by chromatography, spectrometry, or another analysis method, such as the analysis method that is used to analyze the passive sampling device following deployment. For instance, the conditioning treatment can reduce the presence of at least half of the target compounds to an undetectable level, e.g., at least 60% of the target compounds, at least 70%, at least 80%, at least 90%, at least 95%, at least 98%, at least 99%, or at least 99.5% of the target compounds. In some examples, the conditioning treatment removes target compounds and other compounds that may interfere with post-deployment analysis of the passive sampling device.

In some cases, the conditioning treatment includes a solvent conditioning process, e.g., by cleaning the passive sampling device in a solvent. For instance, the passive sampling device can be agitated or sonicated in a solvent above ambient temperature, such as a temperature of at least 33° C., e.g., about 40° C. The agitation can be repeated one or more times. The solvent can be a solvent that is compatible with the impurities to be removed from the passive sampling device, such as a solvent in which the impurities are soluble. For instance, the solvent can be chlorinated or non-chlorinated, miscible, or immiscible in water, and alone or in combination with other solvents like dichloromethane, pentane, iso-octane, acetonitrile, ethyl acetate, hexane, or methanol. In one specific example, the passive sampling device can be agitated in a mixture of ethyl acetate and hexane (1:1, volume:volume (v:v)) for three rounds of agitation and in a mixture of ethyl acetate and methanol (1:1, v:v) for two subsequent rounds of agitation. The solvent-cleaned passive sampling device can be dried, e.g., at elevated temperature or under vacuum or both, to remove traces of solvent from the surface of the passive sampling device.

In some cases, the conditioning treatment includes a heat treatment process, e.g., by heating the passive sampling device under reduced pressure or vacuum to remove volatile or semi-volatile impurities from the passive sampling device. The passive sampling device can be heated to a temperature sufficient to remove impurities from the passive sampling device without melting the silicone. For instance, the passive sampling device is heated to a temperature of at least about 250° C., e.g., about 280-310° C., under a vacuum of less than about 550 mm Hg, e.g., about 530-550 mm Hg. The heat treatment can last for several hours to several days, e.g., at least about 24 hours, at least about 48 hours, or another amount of time.

In some cases, after the passive sampling device has been conditioned, the passive sampling device can be infused with one or more performance reference compounds (304). Performance reference compounds (PRCs) can include labeled compounds, such as deuterated compounds (e.g., pyrene-d10, triclosan-d3, or 1,1-Dichloro-2,2-bis(4-chlorophenyl-d4)ethylene (DDE-d4)), C13 labeled compounds (e.g., fluorene ($^{13}C_6$) or caffeine (trimethyl-$^{13}C_3$)), or compounds labeled with another isotopic label (e.g., D10-pyrene in which the hydrogen atoms are replaced with deuterium or C13-pyrene in which one or more carbon atoms are replaced with C13). PRCs can include non-labeled compounds, such as compounds that are rarely or never found in the environmental media being sampled (e.g., polychlorinated biphenyls congeners 1-3, 10, 14, 21, 30, 50, or 209). Performance reference compounds can be infused into the passive sampling device by soaking the passive sampling device in a solution including the performance reference compound(s), exposing the passive sampling device to an environment that enables compounds to be absorbed into the sampler through passive diffusion. One specific example includes using a solution of a 1:1 mixture (by volume) of methanol:water, but could be done through other aqueous mixtures with miscible solvents. Performance reference compounds may also be directly applied to the wristband. In some cases, no performance reference compounds are infused into the passive sampling device.

The use of a performance reference compound allows for calibration of subsequent analysis of the passive sampling device to control for conditions to which the passive sampling device was exposed. For instance, a known amount of performance reference compound can be infused into the passive sampling device. The diffusion rate of the performance reference compound is known as a function of conditions such as temperature, humidity, or other conditions. Thus, the amount of performance reference compound remaining in the passive sampling device during subsequent analysis of the passive sampling device can be used to account for environmental factors that can cause differences in diffusion rates, such as temperature, humidity, and atmospheric pressure. By coupling the diffusion rate from a performance reference compound with sampler-compound partition coefficients, the amount of compound absorbed in the passive sampling device may be converted to environmental concentrations, e.g., $ng/m^3$ in air, or ng/L in water. For example, pyrene-d10 may be used as a performance reference compound to estimate atmospheric or water concentrations of pyrene and other similar compounds absorbed during deployment.

In some examples, the performance reference compound can be a compound that can act as a sensor during use of the passive sampling device, e.g., to indicate when the passive sampling device has been exposed to a particular environmental compound or to a threshold level of a particular environmental compound. For instance, the performance reference compound can be a compound that undergoes a transformation upon contact with another material (e.g., a particular environmental compound). In some examples, the performance reference compound can change color or undergo a chemical reaction upon contact with another material. The transformation of the performance reference compound can be read visibly (e.g., in the case of a color change) or using a sensor device (e.g., in the case of a chemical reaction).

The conditioned passive sampling device is placed in an airtight, contaminant-free container (306), such as a bag or box. In some examples, the airtight container is a re-sealable polytetrafluoroethylene bag. The airtight container prevents the passive sampling device from sequestering compounds before a user intends to use the passive sampling device. The conditioned passive sampling device can be stored at room temperature, at low temperatures (e.g., about 4° C.), or frozen for long periods of time, e.g., up to several years, prior to use.

When a user intends to use the passive sampling device, he opens the airtight container and places the passive sampling device in the desired environment (308). In some examples, the user can wear the passive sampling device (e.g., when the passive sampling device is a wristband, lapel pin, or other wearable item) such that the passive sampling device can be used to monitor the user's exposure to various compounds. In some examples, the user can place the passive sampling device in room or other area (e.g., by hanging the passive sampling device on a wall or door or resting the passive sampling device on a counter or table) such that the passive sampling device can be used to monitor various compounds present in the room or area.

During use, the passive sampling device passively sequesters compounds to which the device is exposed. For instance, gaseous or vapor phase compounds in the air can diffuse into the passive sampling device, raising the concentration of those compounds in the passive sampling device. In some instances, liquid or solid phase compounds with which the passive sampling device comes into contact can also diffuse into the passive sampling device. Compounds accumulate in the passive sampling device (e.g., in the polymeric material of the passive sampling device) over time, such that a longer exposure of the passive sampling device to an environment will result in a higher level of compounds from the environment being sequestered by the passive sampling device. The amount of each compound sequestered by the passive sampling device thus reflects the degree to which the compound is present in the environment where the passive sampling device was used. Subsequent analysis of the passive sampling device can identify the compounds to which the passive sampling device was exposed and quantify the level of exposure to each of the compounds.

The user keeps track of the amount of time for which he uses passive sampling device (310). In some examples, the user can use the passive sampling device continuously, in which case the user keeps track of the amount of time between when the user starts using the passive sampling device and when the user stops using the passive sampling device. In some examples, the user can use the passive sampling device intermittently, e.g., wearing the passive sampling device only during the workday or only when he enters a particular area of a factory. When the user is not using the passive sampling device, he returns it to an airtight container until he is ready to use it again. In this case, the user keeps track of only the amount of time for which the passive sampling device is actually in use and not the amount of time the passive sampling device is kept in its airtight container.

When the user is finished with the passive sampling device, he seals the passive sampling device into an airtight container (312) until the passive sampling device can be analyzed. For instance, the user can return the passive sampling device to a laboratory for analysis. In some examples, the airtight container in which the passive sampling device is stored after use is the same airtight container in which the passive sampling device was stored initially.

To analyze the passive sampling device, a passive sampling device is cleaned (314) in order to remove surface contamination, such as particulate matter or biofouling resulting from contact with a user's skin. Cleaning can include, e.g., rinsing the passive sampling device with water or an organic solvent, soaking the passive sampling device in a dilute acid, sonicating the passive sampling device, gas purging the passive sampling device, wiping the surface with lint-free tissue, physically removing particulates or surface material with gloved hands, or another cleaning method. The compounds sequestered by the passive sampling device are extracted from the cleaned passive sampling device (316), e.g., using solvent extraction, thermal desorption, or another extraction method.

In some cases, compounds are extracted from the passive sampling device using a solvent extraction process in a solvent in which the targeted compounds are soluble. Solvent extraction can include soaking the passive sampling device in a solvent, Soxhlet extraction, or another approach to solvent extraction such as accelerated solvent extraction. In some cases, passive sampling device can be agitated or sonicated in the solvent. Solvent extraction can be performed at room temperature or at elevated temperature, e.g., at a temperature up to the boiling point of the solvent. Solvent extraction can be performed at atmospheric pressure or at higher pressure. In an example, a passive sampling device is agitated in ethyl acetate to extract the compounds from the passive sampling device into the ethyl acetate. The solvent is reduced using an evaporator and the extract is stored, e.g., at low temperature (e.g., 4° C.) until analysis. After extraction, samples may be further optimized for analytical chemistry techniques through solid phase extraction, gel permeation chromatography, silica columns and liquid chromatography.

The extract is analyzed (318) by chromatography, spectrometry, or another analysis method to identify the compounds present in the extract and to determine an amount of each compound present in the extract. For instance, the extract can be analyzed by gas chromatography-mass spectrometry (GC-MS), liquid chromatography-mass spectrometry (LC-MC), spectrophotometry, electrophoresis, or another analysis method.

In some examples, compounds can be extracted using a solvent that is compatible with multiple types of analysis methods, such as a solvent that is compatible with both GC-MS and LC-MS. For instance, the solvent can be miscible in water or miscible in a solvent mixture used as mobile phases on the LC-MS system, but still volatile enough to help compounds ionize in the gaseous phase on the GC-MS, such as ethyl acetate, acetonitrile, acetone, tetrahydrofuran, isopropanol and others. A solvent that is compatible with both GC-MS and LC-MS can be used because of the wide range of compounds (having a wide range of hydrophobicity) expected to be extracted from the passive sampling device. In some examples, compounds can be extracted using a solvent that is compatible with a specific type of analysis method. For instance, the solvent can be water, an alcohol, hexane, toluene, or another solvent.

In some cases, the compounds are extracted from the passive sampling device through a thermal desorption process. All or a piece of a passive sampling device can be heated under reduced pressure or vacuum to thermally desorb volatile compounds from the passive sampling device. For instance, a passive sampling device can be heated to a temperature greater than about 150° C., e.g., about 180° C., about 200° C., about 220° C., or another temperature up to the melting point of the material of the passive sampling device. During the heating process, nitrogen can be pumped through the heating chambers so that compounds may be collected on desorption tubes, at about 50 mL/min until the programmed temperature is reached. Compounds desorbed from the passive sampling device can be directed to an analysis instrument, such as a mass spectrometer.

Multiple extraction methods can be used on a single passive sampling device. For instance, a wristband can be cut into pieces such that one piece can be treated using solvent extraction and another piece can be treated using thermal desorption.

A passive sampling device or extracts from a passive sampling device can be archived for future analysis (320). For instance, a piece of the passive sampling device or extracts from the passive sampling device can be stored at low temperature (e.g., <0° C.) in an airtight container. Archiving can be useful, e.g., for retrospective analysis of a user's exposure to a compound that had not been screened for in a previous analysis.

In some cases, the passive sampling device is not conditioned prior to use. The passive sampling device or extract can be cleaned prior to analysis. In some examples, solvents can be exchanged into another solvent in order to leave behind unwanted residues or to prepare samples for additional cleaning processes (e.g., hexanes to acetonitrile, acetone to hexane, ethyl acetate to dichloromethane, or another solvent exchange). In some examples, sample extracts can be rinsed with acids (e.g., sulfuric acid) to remove contaminants or to prepare for additional cleaning processes. Other examples of cleaning processes can include, e.g., centrifugation to remove solids or separate immiscible solvent fractions, solid phase extraction techniques (e.g., silica, activated carbon, or ion exchange cartridges), gel permeation or other chromatography techniques, or other approaches to cleaning Examples of silicone cleaning processes without conditioning prior to deployment can be found in Chapter 2.3 Prosthesis extraction, pages 463-464 in "Allan et al., 2013, Should silicone prostheses be considered for specimen banking? A pilot study into their use for human biomonitoring. Environment International 59:462-468," the contents of which are incorporated herein by reference in their entirety.

In some cases, a passive sampling device provided herein can be provided as part of a product package that includes analysis services, archiving services, or both. For instance, when a consumer purchases a passive sampling device, the passive sampling device can be package in a resealable airtight container, such as a polytetrafluoroethylene bag, and shipped to the consumer. Once the consumer is finished wearing or using the passive sampling device, the consumer can place the passive sampling device back in the same airtight container or in another container and return the passive sampling device to an analysis laboratory. The consumer's purchase of the passive sampling device can include a contract for analysis services, such as testing for a specific list of compounds or open-ended testing for any identifiable compound and reporting of the test results. The consumer's purchase can include archiving services, e.g., in case the customer desires additional analysis at a future date.

Passive sampling devices provided herein can be small and light enough that shipping costs are minimal. For instance, a passive sampling device can be sized and dimensioned such that a standard first-class stamp can cover postage costs. A customer's purchase of a passive sampling device can include shipping to the customer, return shipping to the analysis laboratory, or both.

Examples of passive sampling devices can be found in O'Connell, S; Kincl, L. D.; Anderson, K. A., Silicone Wristbands as Personal Passive Samplers. *Environ. Sci. Technol.* 2014, 48, 3327-3335, the contents of which are incorporated here by reference in their entirety.

EXAMPLES

The following examples demonstrate example approaches to conditioning, use, and analysis of silicone wristbands used as passive sampling devices. For the examples described here, all solvents used were Optima-grade (Fisher Scientific, Pittsburgh, Pa.) or equivalent, and all laboratory glassware and other tools were solvent-rinsed before use. Any water used in initial conditioning or post-deployment cleaning of the wristbands was filtered through a Barnstead D7389 purifier (Dubuque, Iowa).

Example 1

Wristband Conditioning

Conditioning of wristbands can remove impurities, such as oligomers or other material that might interfere with future chemical analysis of the wristbands.

Commercially available silicone bracelets were purchased in two sizes (width 1.3 cm and 2.5 cm, inner diameter 6.4 cm and 6.7 cm, respectively; 24hourwristbands.com, Houston, Tex.). The wristbands were weighed prior to processing. The small wristbands (1.3 cm width) had similar weights regardless of pigmentation (orange: $5.67\pm0.02$ g; clear: $5.68\pm0.02$ g; orange/white: $5.71\pm0.02$ g; n=15 for each color). The large wristbands (2.5 cm width) weighed $10.38\pm0.02$ g. Only the small wristbands were used for quantitative work described below.

In an example of a solvent conditioning process, $\leq 65$ g of silicone wristbands were conditioned in 800 mL of mixed solvent for five exchanges. A mixture of ethyl acetate and hexane (1:1, volume:volume (v:v)) was used for the first three exchanges, and a mixture of ethyl acetate and methanol (1:1, v:v) was used for the last two exchanges, all at 40° C. Each exchange was carried out for a minimum of 2.5 hours under agitation of 60 rotations per minute (VWR orbital shaker, Radnor, Pa.). After the five exchanges were completed, the solvent-cleaned wristbands were placed in stainless steel canisters (AEB Kegs, Delebio S O, Italy) and dried under polyurethane foam (PUF) filtered vacuum for up to three days. Dried wristbands were stored in either amber glass jars or in polytetrafluoroethylene (PTFE) airtight bags at 4° C. until needed. For comparison, silicone wristbands were also conditioned with five exchanges of ethyl acetate and methanol (1:1, v:v) under similar conditions except exchange times were carried out over 24 hours rather than 2.5 hours. Lower oligomer background was observed with both shorter times per exchange period and by using hexanes.

The conditioned wristbands were subjected to solvent extraction (described below) and gas chromatography-mass spectroscopy (GC-MS) was performed on the extracts. Referring to FIGS. 4A and 4B, total ion chromatograms of the wristband extracts are shown for the wristbands that had been conditioned in ethyl acetate and methanol (FIG. 4A) and the wristbands that had been conditioned in ethyl acetate, methanol, and hexane (FIG. 4B). The chromatograms are scaled equally to show differences. FIGS. 4A and 4B show that the addition of hexane as a conditioning solvent drastically reduces the total background interference from impurities in the silicone.

The wristbands conditioned with ethyl acetate, methanol, and hexane were infused with PAH compounds and OPAH compounds and processed using solvent extraction as described below. FIG. 4C shows the total ion chromatogram of a GC-MS analysis of the resulting extract. Salient peaks are labeled with the corresponding PAH or OPAH compound. The chromatogram enabled the quantitation of the PAH and OPAH compounds within 26% of the true value, demonstrating that the solvent conditioning process removes enough impurities to allow for accurate quantification of contaminant compounds sequestered by the wristband.

In an example of a heat conditioning process, silicone wristbands were placed in large (12 L) round bottom flasks under vacuum (530-550 mm Hg) and heated to 280-300° C. for 48 hours using heating manifolds.

Heat conditioning of wristbands results in a measurable reduction in weight of the wristband. Table 1 shows the percentage weight reduction for each of twelve silicone wristbands treated with heat conditioning. The percent weight reduction of the wristbands following heat conditioning ranged from 0.22% to 3.28%, with an average weight reduction of 1.67%. Similar results were also observed for wristbands treated with a solvent conditioning process; the average percent weight reduction was 2.45% following one round of solvent treatment.

TABLE 1

Weight reduction of wristbands following heat conditioning.

| | Untreated WBs (grams) | Solvent-free Conditioned WBs (grams) | Silicone removed (grams) | Percent loss |
|---|---|---|---|---|
| | 4.710 | 4.699 | 0.011 | 0.22% |
| | 4.692 | 4.664 | 0.029 | 0.61% |
| | 4.733 | 4.584 | 0.149 | 3.14% |
| | 4.670 | 4.617 | 0.053 | 1.12% |
| | 4.741 | 4.596 | 0.145 | 3.06% |
| | 4.740 | 4.584 | 0.156 | 3.28% |
| | 4.733 | 4.611 | 0.122 | 2.57% |
| | 4.685 | 4.622 | 0.063 | 1.34% |
| | 4.703 | 4.678 | 0.026 | 0.54% |
| | 4.711 | 4.601 | 0.110 | 2.34% |
| | 4.681 | 4.668 | 0.013 | 0.28% |
| | 4.707 | 4.635 | 0.071 | 1.51% |
| Average | 4.709 | 4.630 | 0.079 | 1.67% |
| Minimum | 4.670 | 4.584 | 0.011 | 0.22% |
| Maximum | 4.741 | 4.699 | 0.156 | 3.28% |

Figure 5:
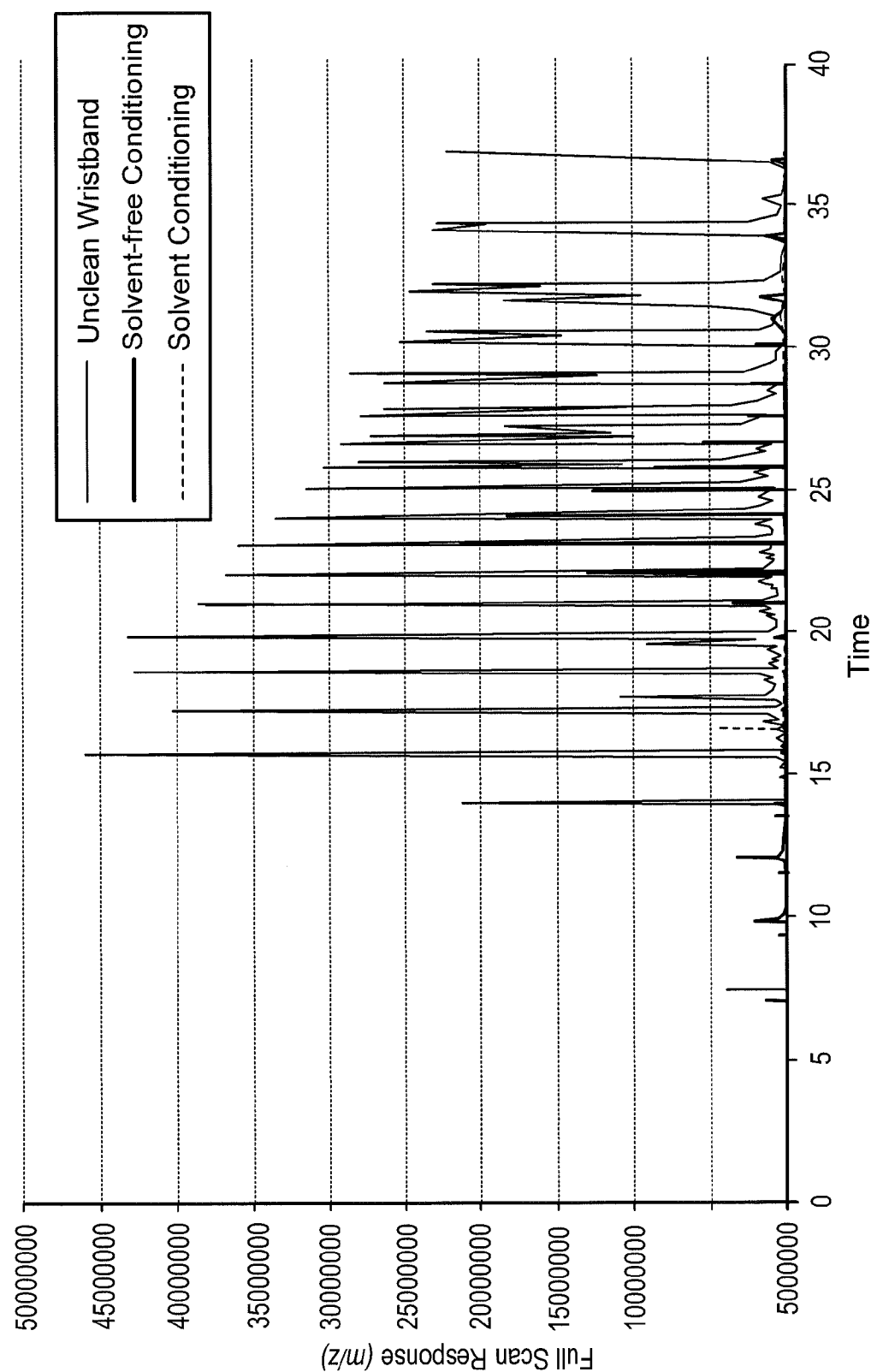
FIG. 5 is a chromatogram of wristband extracts.

FIG. 5 shows chromatograms for wristbands prior to conditioning and following heat and solvent conditioning processes using a GC-MS in full scan mode (50-500 m/z). The heat conditioning process involved treating the wristbands at 325° C. for 6 days under vacuum. The reduction of peaks corresponding to various types of siloxane chains is evident in both the heat conditioned and the solvent conditioned samples. Table 2 shows quantitative data obtained from the chromatograms of FIG. 5, indicating that a significant portion of siloxanes and other impurities are removed from the wristbands during the conditioning process.

TABLE 2

Quantitative purity data for uncleaned and conditioned wristbands.

| WB Treatment | Total Area | % Siloxanes left* | % siloxanes and other impurities removed* |
|---|---|---|---|
| Solvent | 2.95E+07 | 0.44% | 99.56% |
| Solvent-free^ | 2.38E+08 | 3.53% | 96.47% |
| Unclean | 6.74E+09 | | |

*relative to unclean WB total area
^325° C. for 6 days under vacuum

Conditioned wristbands were chemically screened for the presence of target impurities to determine the effectiveness of the conditioning processes at removing the target impurities. Screening was conducted for 1182 compounds including pesticides, endocrine disrupting compounds (EDCs), breakdown products of pesticides or EDCs, personal care products, PAHs, OPAHs, and PCBs. Only a small number of target impurities were detected in the conditioned wristbands. Table 3 lists the target impurities that were detected in three of the screened conditioned wristbands.

TABLE 3

Target impurities detected in three conditioned wristbands (WB).

| WB1 | WB2 | WB3 |
|---|---|---|
| Di-n-butylphthalate | Bis(2-ethylhexyl)phthalate | Butylated hydroxyanisole |
| Bis(2-ethylhexyl)phthalate | Exaltolide | Di-n-butylphthalate |
| Naphthalene | Di-n-nonyl phthalate | Bis(2-ethylhexyl)phthalate |
| Exaltolide | | Exaltolide |
| Di-isobutyl phthalate | | Di-n-nonyl phthalate |
| Di-n-nonyl phthalate | | |

Wristbands treated with both the solvent conditioning process and the heat conditioning process were infused with surrogate standards 4,4-dibromooctafluorobiphenyl, tetrachloro-m-xylene, PCB 100, and PCB 209 (the 4 highest peaks, left to right in FIG. 6A), and analyzed using gas chromatography-electron capture detection.

Referring to FIG. 6A, chromatograms for wristbands treated with solvent conditioning and heat conditioning are shown using electron capture detection. Surrogate standards (indicated by the peaks) are readily seen, indicating that both solvent conditioning and heat conditioning effectively remove impurities from the wristbands under this detection method. Referring to FIG. 6B, a zoomed in view shows that the heat conditioning removes impurities from the wristbands slightly more effectively than solvent conditioning.

Prior to deployment, two wristbands from a batch of conditioned silicone wristbands were assessed to ensure that the cleaning processes were adequate for future quantitative analysis of the wristbands of the batch. If the highest background peak of the wristbands had an area less than 15-fold of a spiked internal standard of 500 ng/mL, then the background level of the conditioned wristbands was considered adequate for deployment.

Example 2

Solvent Extraction and Analysis

Wristbands returned from deployment were rinsed twice with purified water. The wristbands were then rinsed with isopropyl alcohol for less than 10 seconds to reduce water residue on the surface of the wristbands. The three rinses removed much of the surface particulate matter. Water was not replaced during cleaning of multiple wristbands because the fugacity of the hydrophobic compounds sampled by the wristband does not drive those compounds into aqueous solution. Isopropyl alcohol was replaced for each wristband. No carry-over of surrogates standards such as naphthalene-d8, acenaphthylene-d8, phenanthrene-d10, fluoranthene-d10, chrysene-d12, benzo[a]pyrene-d12, benzo[ghi]perylene-d12 was observed during post-deployment cleaning.

In one example of an extraction process, compounds sampled by the wristband were extracted from the wristband by a two-round solvent extraction. The wristband was agitated in 100 mL of ethyl acetate on an orbital shaker (VWR) at 60 rotations per minute for 2 hours. The wristband was then removed from the ethyl acetate and agitated in 100 mL of ethyl acetate at 60 rotations per minute for another 2 hours. Both rounds of extraction were combined and reduced to 1 mL (measured with premarked glassware) with closed-cell evaporators (Biotage LLC, Charlotte, N.C.). Extracts were stored in amber chromatography vials at 4° C.

The efficiency of the extraction method was determined by quantitatively analyzing subsequent rounds of extraction (100 mL of ethyl acetate) from pre-cleaned silicone wristbands that had been infused with four deuterated polycyclic aromatic hydrocarbons (PAHs). Acenaphthylene-D8, fluorine-D10, phenanthrene-D10, and pyrene-D10 were pipetted into a 1 L jar filled with approximately 50-100 g of silicone in a methanol/water (1:1, v:v) solution. The mixture was allowed to equilibrate for three days, after which time the wristbands were dried as described above. Three consecutive rounds of extraction in 100 mL of ethyl acetate at 60 rotations per minute for either 2 hours or 24 hours (for a total of either 6 hours or 72 hours) were used to examine extraction efficiency.

Figure 7:
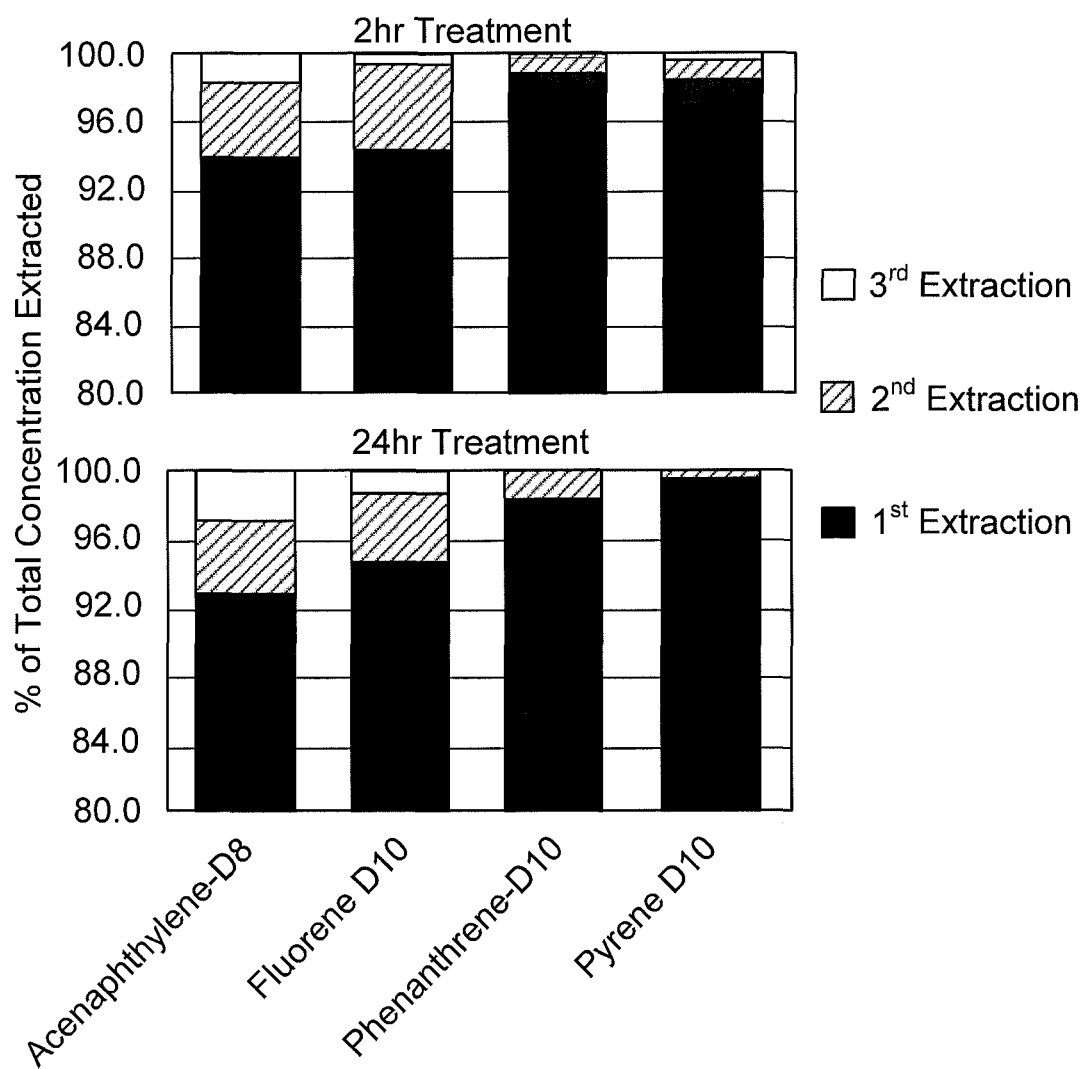
FIG. 7 is a plot of compounds extracted from wristbands during subsequent extractions.

FIG. 7 shows the percentage of the total concentration of each deuterated PAH extracted for each round of extraction. The graphs show the average percentages across three samples (n=3). Over 90% of the total amount of each deuterated PAH was extracted in the first round of ethyl acetate extraction. Less than 6% and less than 5% were extracted in the second and third round of extraction, respectively.

The variability of infused wristbands used for the deuterated PAH experiments was less than 13% (relative standard deviation) across all extraction times and compounds. PAHs with lower hydrophobicity had lower extraction efficiency after the first round of solvent extraction, but all four compounds had at least 96% of the final extracted amount extracted after two rounds of extraction. The amounts extracted in the 2 hour extractions did not differ from the amounts extracted in the 24 hour extractions (892±60 ng/mL or 878±47 ng/mL, respectively, p=0.78), indicating that 2 hours is sufficient for compound extraction from the wristbands.

The extracts were analyzed for 1182 chemicals using retention time locking automatic mass spectral deconvolution and identification software (AMDIS) on an Agilent 5975B gas chromatograph-mass spectrometer (GC-MS) with a DB-5MS column (Agilent) at an electron impact mode of 7.0 eV in selective ion mode. The spectra acquired from the wristbands were compared against libraries of compounds that included pesticides, polychlorinated biphenyls (PCBs), parent and substituted PAHs, pharmaceuticals, phthalates, and other compounds. Prior to PAH and OPAH analyses, perylene-d12 and fluorofluorenone-$C^{13}$, respectively, were spiked at 500 ng $mL^{-1}$ as internal standards.

For PAHs, sample concentrations were determined by the relative response of deuterated surrogates to target analytes in a 9-point calibration curve with correlation coefficients for each analyte greater than 0.98. OPAHs were quantitated with a 9-point calibration curve with correlation coefficients greater than 0.99, but were not recovery corrected due to lack of availability of appropriate surrogates.

Over 40% of analysis samples were for quality control (QC) purposes. QC samples included instrument check standards that were run before and after each set of 10 or fewer samples; and laboratory solvent blanks Analysis was conducted on samples only if the PAH and OPAH levels in the check standards were within 20% of the true values. Non-deployed wristbands were used during post-deployment cleaning to ensure that there was no carry-over of compounds or contamination between samples.

For AMDIS analysis, only compounds above a 60% mass spectral match were considered for chemist review. Deconvoluted results were compared against reference spectra for each target analyte. If multiple lines of evidence for an analyte (e.g., correct ratios of ions, larger ions more representative of the parent ion, or retention time match) were present in a spectrum of a sample, then the analyte was considered to be identified in the sample. Any compounds identified in controls or laboratory blanks were removed from the initial ambient demonstration since AMDIS results are descriptive as presented.

Example 3

Thermal Desorption and Analysis

Volatile compounds can be extracted and analyzed by direct thermal desorption from silicone wristbands. As part of the instrumental development method, the compounds listed in Table 3 were pipetted onto the surface of silicone wristbands and were allowed to dry at room temperature. Then, the compounds were desorbed off of the wristbands at one of 180° C., 200° C., or 220° C. at a 50 mL/min flow rate of nitrogen until the maximum temperature was reached (25, 30, and 39 minutes, respectively).

To compare against a standard, compounds listed in Table 3 were injected onto a desorption tube, and then desorbed out of the tube into a gas chromatograph-mass spectrometer. Table 3 lists the percent of each compound at one of the above temperatures (180° C., 200° C., and 220° C.) considered optimal (e.g. 200° C.), determined by comparing the amount desorbed off of the surface of silicone wristbands to the standard injection which was considered to be 100%. Considering all volatile organic compounds, an average of 90% were present as compared with the direct injection onto the desorption tube at 200° C. These values are also shown as a bar graph in FIG. 8.

TABLE 3

Compounds analyzed via thermal desorption off of wristbands compared to a standard.

|  | Compounds | 200° C. |
|---|---|---|
| 1 | Benzene | 24 |
| 2 | Benzene, chloro- | 70 |
| 3 | Ethylbenzene | 74 |
| 4 | m and p-Xylene | 74 |
| 5 | o xylene | 73 |
| 6 | Styrene | 75 |
| 7 | Benzene, (1-methylethyl)- | 78 |
| 8 | Benzene, bromo- | 91 |
| 9 | Benzene, propyl- | 113 |
| 10 | Benzene, 1-chloro-2-methyl- | 91 |
| 11 | Benzene, 1,3,5-trimethyl- | 104 |
| 12 | Benzene, 1-chloro-4-methyl- | 90 |
| 13 | Benzene, tert-butyl- | 91 |
| 14 | Benzene, 1,2,4-trimethyl- | 94 |
| 15 | Benzene, (1-methylpropyl)- | 88 |
| 16 | Benzene, 1-methyl-3-(1-methylethyl)- | 92 |
| 17 | Benzene, 1,3-dichloro | 94 |
| 18 | Benzene, 1,4-dichloro- | 94 |
| 19 | Benzene, butyl- | 98 |
| 20 | Benzene, 1,2-dichloro- | 90 |
| 21 | Benzene, 1,2,4-trichloro- | 188 |
| 22 | Naphthalene | 104 |
| 23 | Benzene, 1,2,3-trichloro- | 88 |

Example 4

Ambient Deployment of Wristbands

To study the ability of silicone wristbands to sequester organic compounds, 22 study participants wore a wristband continuously for 30 days including during bathing, sleeping, and other activities. Some participants wore multiple wristbands. We sometimes refer to the wristbands in this example as ambient wristbands.

A total of 30 wristbands, conditioned as described above, were placed into three amber jars, and metal tongs were used by participants to take one or two wristbands to wear. At the end of the 30-day period, each wristband was collected in a small (250 mL) amber jar and stored at −20° C. until post-deployment cleaning and solvent extraction. Three non-deployed wristbands were placed into amber jars and stored at room temperature to serve as controls against potential laboratory or processing contamination.

Table 4 lists the compounds identified from the ambient wristband extracts and the number of wristbands (WBs) in which compound was identified. 49 different compounds were identified, representing a wide diversity of bioavailable compounds. The log $K_{ow}$ properties of the identified compounds spanned a wide range of values, from a minimum log $K_{ow}$ value of −0.07 (caffeine) to a maximum $K_{ow}$ value of 9.49 (tri(2-ethylhexyl) phosphate).

TABLE 4

Compounds identified in ambient wristband extracts.

| Compounds | log $K_{ow}$ | Number of wristbands |
|---|---|---|
| PAHs | | |
| 1-methylnaphthalene | 3.87 | 16 |
| anthracene | 4.45 | 5 |
| fluorene | 4.18 | 5 |
| 1,6-dimethylnaphthalene | 4.26 | 4 |
| 1-methylphenanthrene | 5.08 | 3 |
| 1,2-dimethylnaphthalene | 4.31 | 2 |
| Acenaphthylene | 4.07 | 1 |
| pyrene | 4.88 | 1 |
| retene | 6.35 | 1 |
| Consumer products | | |
| tonalide | 5.70 | 20 |
| carvone | 3.07 | 14 |
| triclosan | 4.76 | 9 |
| caffeine | −0.07 | 6 |
| nicotine | 1.17 | 4 |
| eugenol | 2.49 | 4 |
| celestolide | 5.93 (est) | 2 |
| musk ketone | 4.30 | 1 |
| phantolide | 5.85 (est) | 1 |
| phthalimide | 1.15 | 1 |
| Pesticides | | |
| benzyl benzoate | 3.97 | 18 |
| N,N-diethyl-m-toluamide | 2.02 | 11 |
| promecarb artifact | 3.52 (est) | 6 |
| methoprene | 5.50 | 5 |
| Fipronil | 4.00 | 3 |
| fipronil-sulfone | 4.42 (est) | 2 |
| fipronil, desulfinyl- | 4.22 (est) | 1 |
| trifluralin | 5.34 | 1 |
| Phthalates | | |
| diethyl phthalate | 2.47 | 23 |
| butyl benzyl phthalate | 4.73 | 19 |
| di-n-octyl phthalate | 8.10 | 11 |
| di-n-hexyl phthalate | 6.825 | 9 |
| dicyclohexyl phthalate | 6.20 (est) | 6 |
| dimethylphthalate | 1.60 | 5 |
| Industrial compounds | | |
| benzophenone | 3.18 | 19 |
| triphenyl phosphate | 4.59 | 15 |
| tris(2-butoxyethyl) phosphate | 3.75 | 4 |
| tributyl phosphate | 4.00 | 5 |
| 2-methylphenol | 1.95 | 4 |
| tris(2-chloroethyl) phosphate | 1.44 | 3 |
| tris(2-ethylhexyl) phosphate | 9.49 | 3 |
| o-tricresylphosphate | 6.34 | 2 |
| triethylphosphate | 0.80 | 2 |
| o-phenylphenol | 3.09 | 2 |
| m-cresol | 1.96 | 2 |
| p-tricresylphosphate | 6.34 | 1 |
| 2,4-dimethylphenol | 2.30 | 1 |
| 4-methylphenol | 1.94 | 1 |

The compounds identified from the ambient wristband extracts included PAHs, consumer and personal care products, pesticides, phthalates, and other industrial compounds such as compounds used as flame retardants or plasticizers or used in synthetic materials manufacturing. The two most frequently detected compounds were diethyl phthalate (detected in all 23 wristbands) and tonalide (detected in 20 of 23 wristbands), both of which are used in personal care products such as fragrances or cosmetics. Home-use pesticides such as N,N-diethyl-m-toluamide (DEET) and fipronil (pet flea medicine) and consumer product ingredients such as caffeine and nicotine were detected in several samples.

Figure 8:
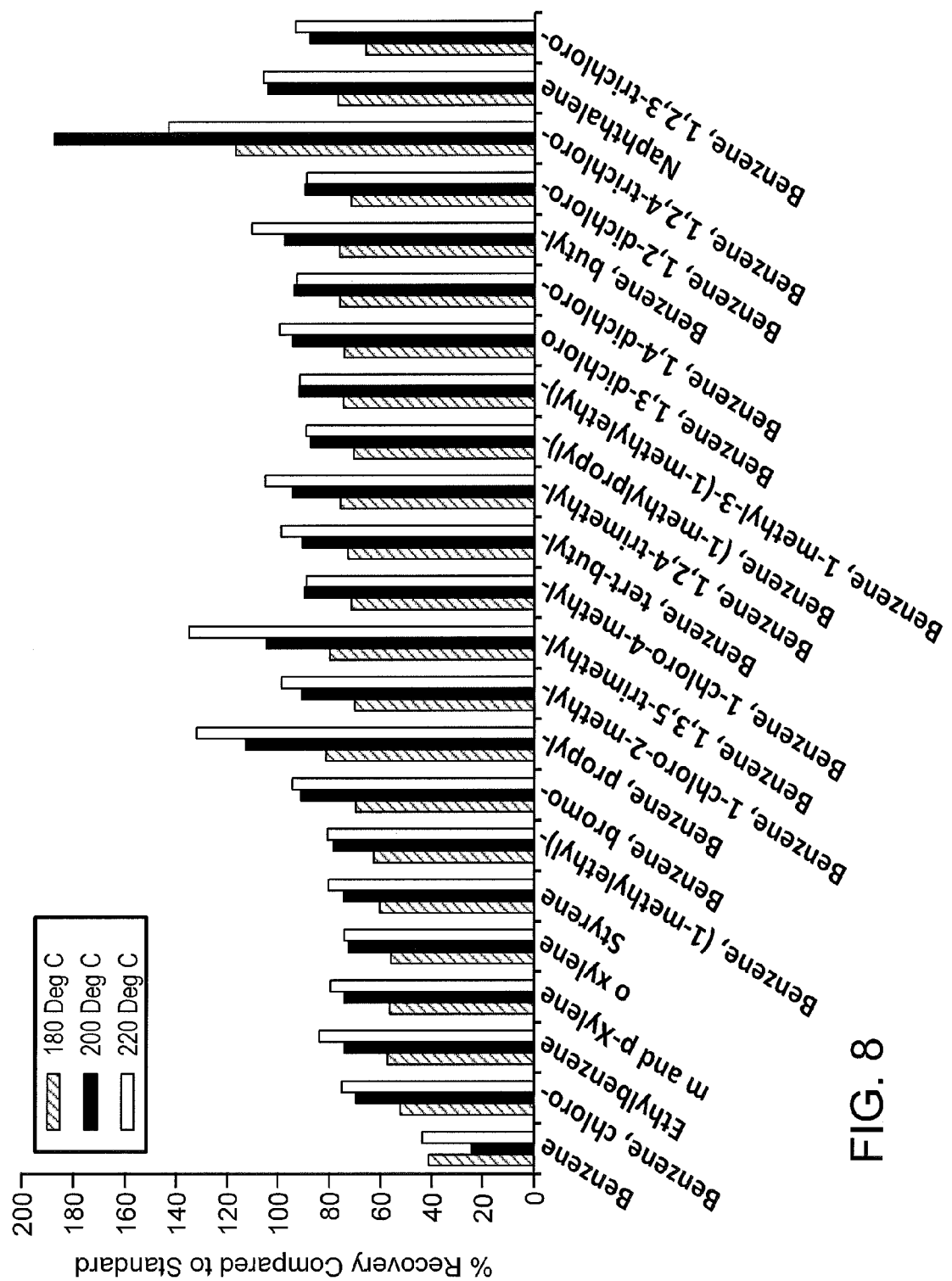
FIG. 8 is a plot of thermal desorption of compounds on wristbands.
Figure 9:
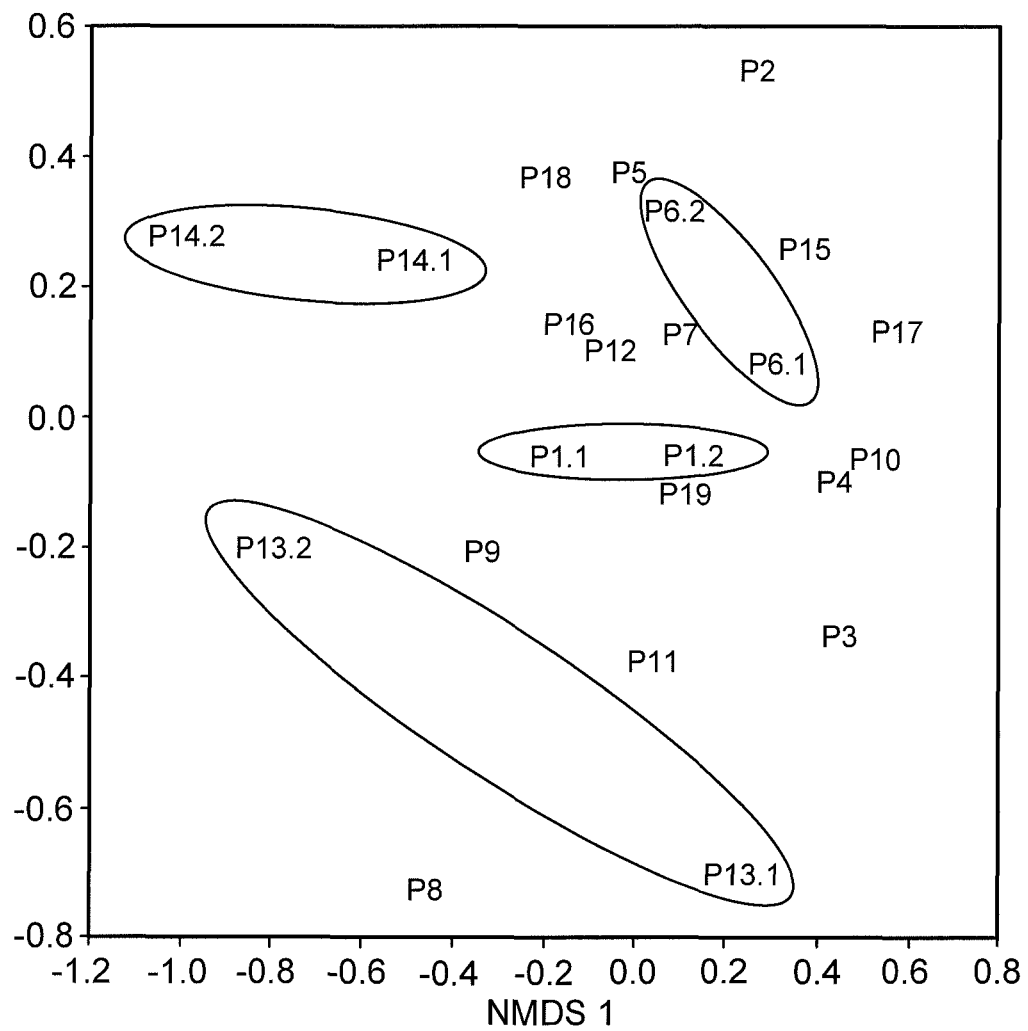
FIG. 9 is a plot of ambient wristband data.

Referring to FIG. 9, an analysis of the results of the ambient wristband analysis using a nonmetric multidimensional scaling model indicate that the results different across individual participants of the study. FIG. 8 is a graphical representation of binary data from the 49 compounds identified in the study. Positively identified compounds were assigned binary identifiers and used in a nonmetric multidimensional analysis to determine whether each participants wristband reflected a unique exposure profile or whether all wristbands in the study sequestered the same or similar number and type of compounds. In FIG. 9, points corresponding to wristbands worn by the same participant are circled. The spatial differences among results on the graph indicate that some at least some exposures were unique, e.g., between wristband 8 and wristband 2.

The total ion chromatogram of wristbands 13.1 and 13.2 (both worn by a single participant) had a particularly high number of peaks that is believed to have resulted from skin contact. It is believed that the relatively poor resolution on the graph of wristbands worn by a single participant may be due at least in part to interferences from month-long skin contact or from an earlier cleaning process. Reducing skin contact can reduce the presence of skin compounds such as squalene and free fatty acids on the wristband, which can in turn enable further enhancements in compound detection.

Multivariate statistics were performed on the results of the ambient wristband analysis using R statistical software (R development core team, Vienna, Austria). Identification data for the wristbands were converted into binary values, and a nonmetric multidimensional scaling model was used to graphically represent the data with Jaccard distance.

Example 5

Wristband Deployment in an Occupational Setting

Silicone wristbands were worn by roofers working with hot asphalt to evaluate the ability of the wristbands to sequester compounds in an occupational setting. The exposure of the roofers to PAH was determined through post-deployment analysis of the wristbands.

To evaluate the effect of skin contact on the accuracy of the wristband analysis, each roofer wore three designs of silicone wristband simultaneously: a single wristband worn around the wrist, a cut wristband pinned as a lapel onto a shirt collar, and a stacked wristband in which an inner silicone band protected an outer wristband (the analyte wristband) from sweat, oil, or other potential contaminants from skin contact. We refer to these three configurations as the single, lapel, and stacked configurations, respectively.

Prior to deployment, the silicone wristbands were conditioned as described above and placed into a PTFE bag. Nitrile gloves were used when handling the wristbands. After completion of the deployment, the wristbands were stored at 4° C. until solvent extraction and analysis was performed.

In a first deployment setting (which we sometimes call the rooftop worksite), three workers wore the single and lapel configurations for both a single day (approximately 8 hours) and for a representative workweek (approximately 32-39 hours) while refurbishing a roof at an active worksite, and the stacked configuration for the representative workweek. Both the single day and workweek deployments began on the same day. For the workweek deployment, the wristbands were returned to the PTFE bag after each work day. One day at the rooftop worksite included approximately four hours tearing down an old roof and approximately four hours applying asphalt to create a new roof.

In a second deployment setting (which we sometimes call the training site), five pre-apprentice roofers wore the single, lapel, and stacked configurations during an 8-hour shift at a training facility. At the training facility, roofers spent 8 hours training and applying hot mopping-grade asphalt on a practice surface.

Following exposure, the wristbands were exposed to a solvent extraction process and the extract was analyzed as described above. The extracts from wristbands worn at both the rooftop worksite and the training site showed measurable levels of PAHs, 12 of which are listed on the Environmental Protection Agency (EPA) priority list. In addition, two OPAHs (benzofluorenone and fluorenone) were detected at quantifiable levels at both sites. OPAHs are not typically monitored in asphalt exposures. These results represent evidence of a potential data gap in occupational exposure monitoring.

Figure 10A:
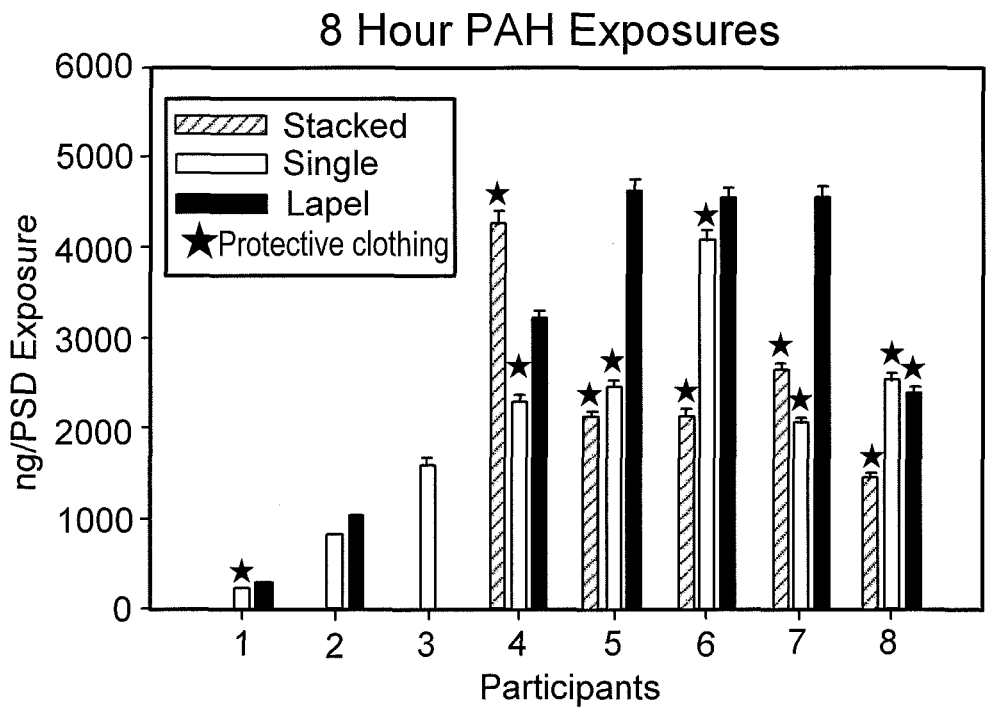
FIGS. 10A and 10B are plots of occupational wristband data.
Figure 10B:
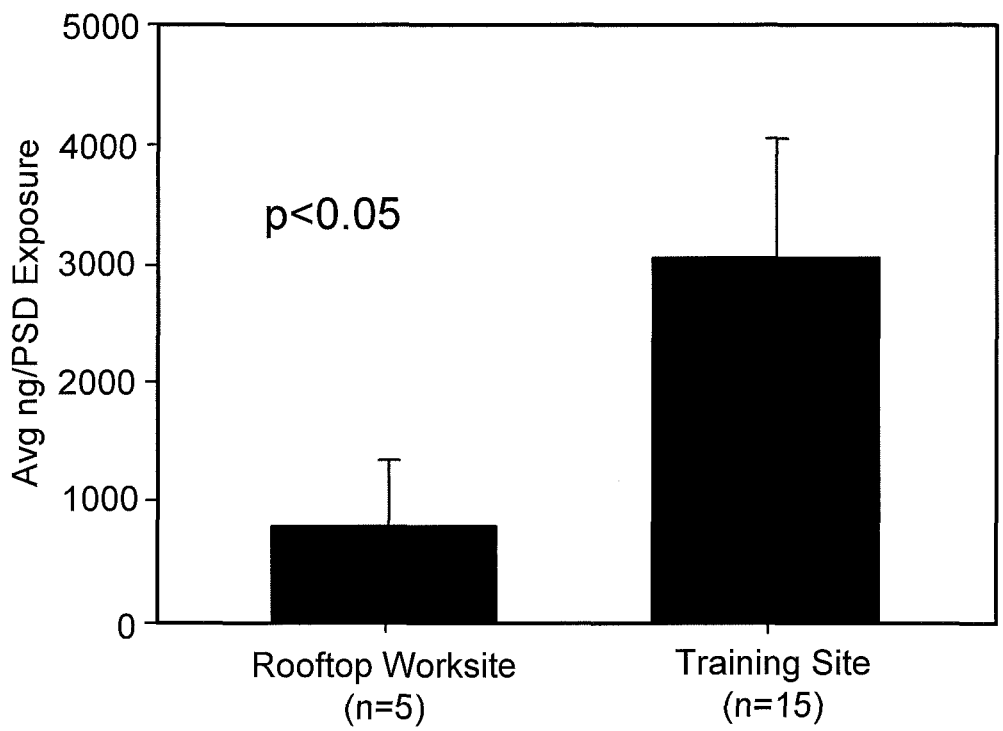

FIGS. 10A and 10B show results of the analysis of the extracts from wristbands work for a single (8 hour) day from both the rooftop worksite and the training site. FIG. 10A shows the results for each individual participant, and FIG. 10B shows the average results for all participants at each site.

Referring specifically to FIG. 10A, the total of all PAHs measured in each wristband ranged from 230 ng to 4600 ng. Concentrations of individual PAH compounds exceeded the instrument detection limit by a factor of between 2 and 1400. These results indicate that the wristbands can be useful for sensitive detection even when deployed for only 8 hours of exposure. Individual PAH surrogate recoveries ranged from 53% to 122% (average 91%, median 94%) and OPAH surrogate recoveries ranged from 64% to 120% (average 83%, median 82%). These recoveries indicate adequate laboratory processing during wristband extractions. The standard deviations shown in FIG. 10A were derived from non-deployed wristbands representing laboratory and instrument variability spiked with all target PAHs (average RSD 2.30%). The stars represent wristbands that were reported as covered with protective clothing during exposure.

Extracts from control wristbands had less 11 ng of total PAHs measured. Individual PAH compounds were below the detection limit for 31 of the 33 PAHs measured; only naphthalene and 2-methylnaphthalene were detected in the control extracts. Levels of these two PAHs were negligible, considering that the average background signal from each of these two PAHs was nominally at least 3 times less than the PAH level detected in the extracts from the deployed samples. There were no detectable OPAH compounds in any control extract.

FIG. 10B shows the average PAH measured in all wristband configurations for all participants at each site. The overall average exposure differed significantly between sites (p<0.05). The standard deviations shown in FIG. 10B are the result of all results from all wristband configurations from all participants at each site.

Figure 11:
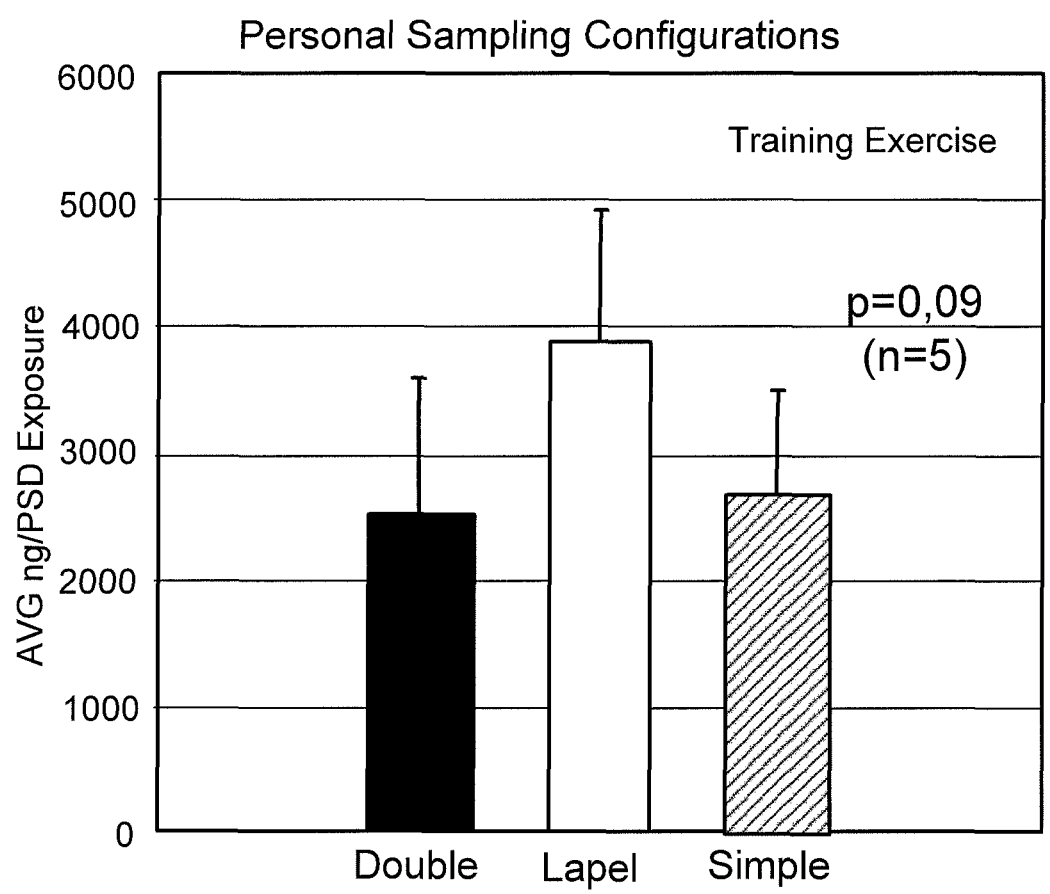
FIG. 11 is a plot of occupational wristband data.

While chromatography analysis was easier to interpret for the lapel and stacked configurations, PAHs and OPAHs were identified and accurately quantified in all three wristband configurations at all exposure durations. Referring to FIG. 11, results from each wristband configuration were pooled to determine any differences in compound sequester or extraction. No statistical significance was observed between configurations (n=5, p=0.09, power<0.8).

Referring again to FIG. 10A, although the differences between configurations were not statistically significant, in some cases (for participants 5 and 7) lower PAH and OPAH concentrations were observed in the extracts from the single and stacked configuration wristbands than from the lapel configuration wristbands. Participants 5 and 7 reported wearing their single and stacked configuration wristbands under protective clothing and wearing the lapel configuration wristband outside of the protective clothing. Participant 8, whose lapel configuration wristband showed lower PAH and OPAH concentrations than observed in the lapel configuration of other participants, reported that his lapel configuration wristband was covered with protective clothing.

These variations may indicate that clothing or other coverings may restrict air flow in the vicinity of the wristband, thus changing the micro-environment around the wristband and limiting the level of exposure relative to that of a non-covered wristband. However, not all variations in concentration can be explained by the presence of protective clothing. For instance, participant 4 reported that his stacked configuration wristband was covered, yet the PAH and OPAH concentrations from that wristband are higher than the PAH and OPAH concentrations from the other wristband configurations worn by participant 4.

Referring to FIGS. 12A-12D, the temporal sensitivity of the wristbands was analyzed by studying the extracts from the wristbands worn for a single, 8-hour day and the wristbands worn for an entire workweek at the rooftop worksite.

Figure 12A:
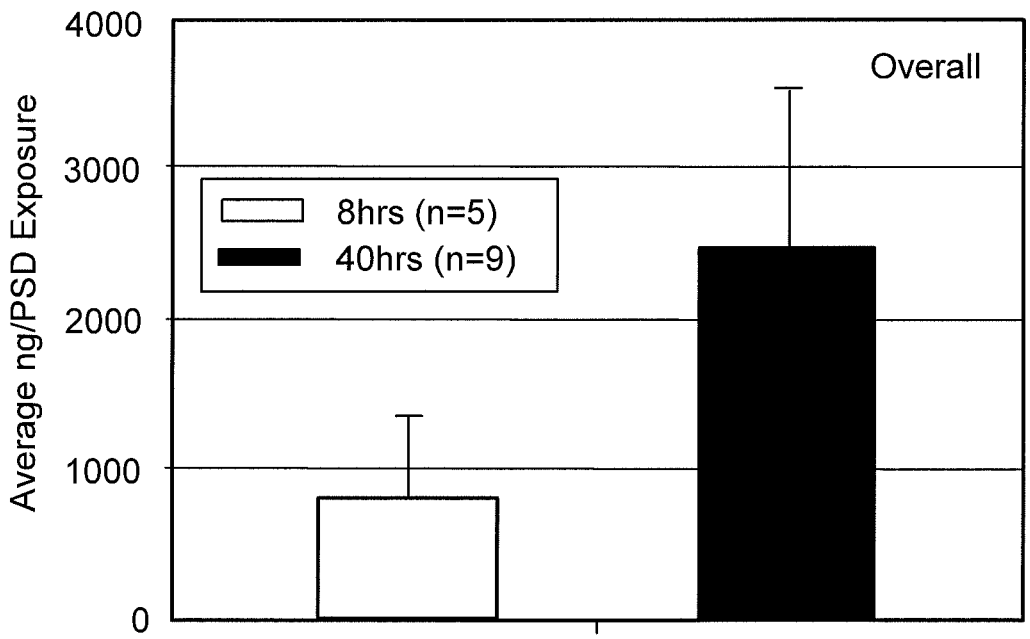
FIGS. 12A-12D are plots of occupational wristband data.

FIG. 12A shows the average PAH measured in all wristband configurations for all participants for each time period. The overall average exposure differed significantly between the single day exposure and the workweek exposure (p<0.05). The standard deviations are the result of all results from all wristband configurations from all participants for each time period.

Figure 12B:
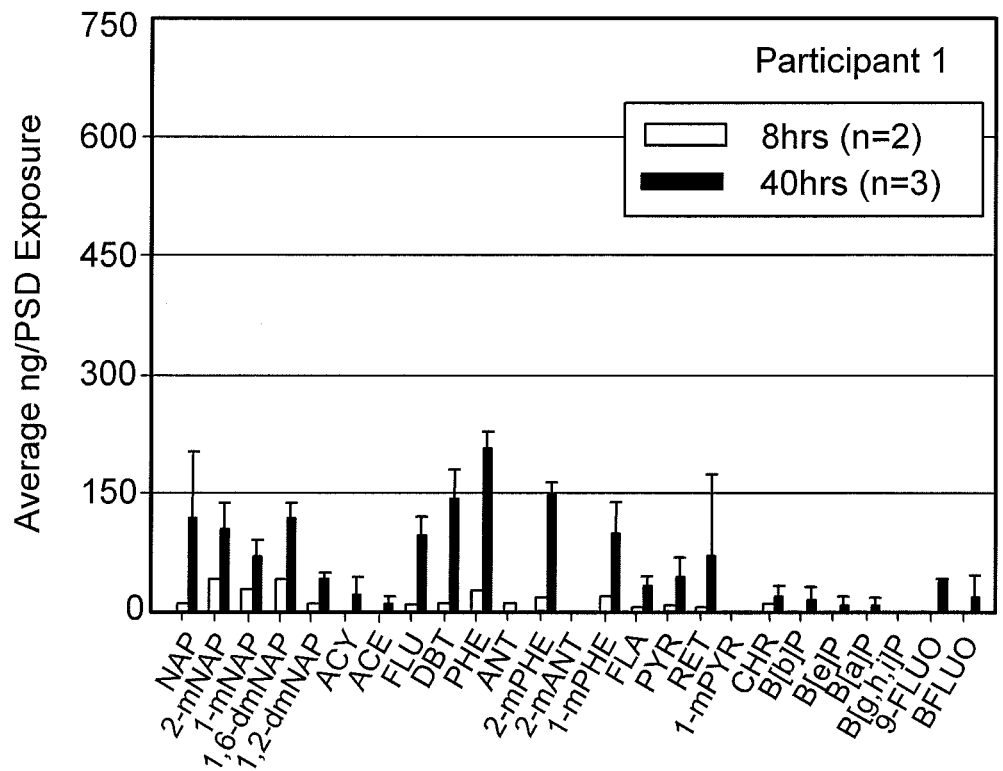
Figure 12C:
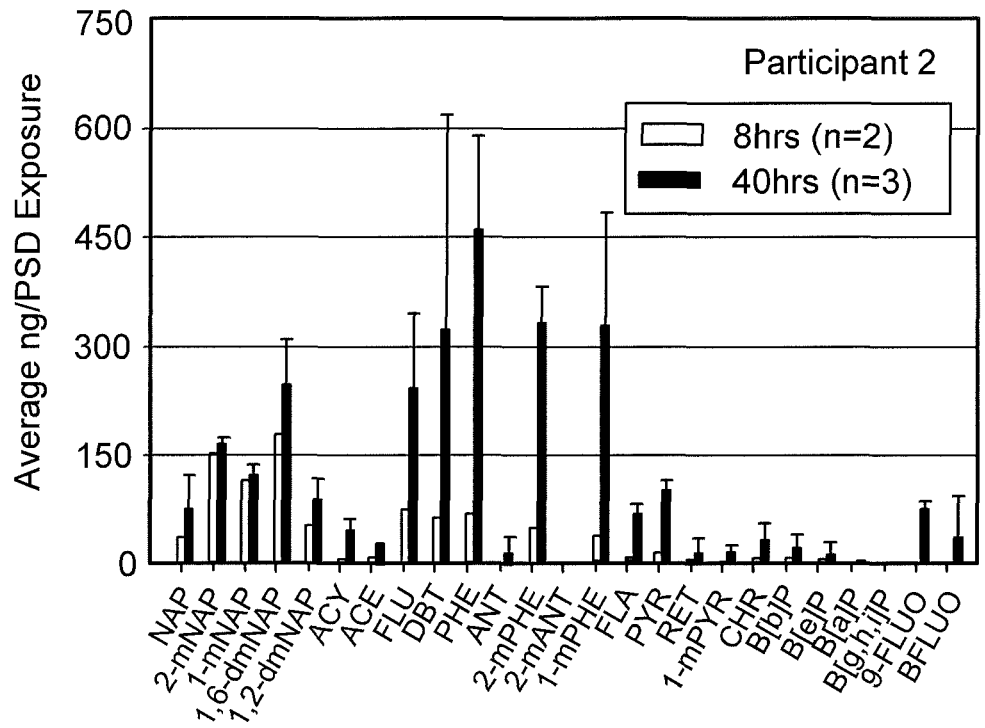
Figure 12D:
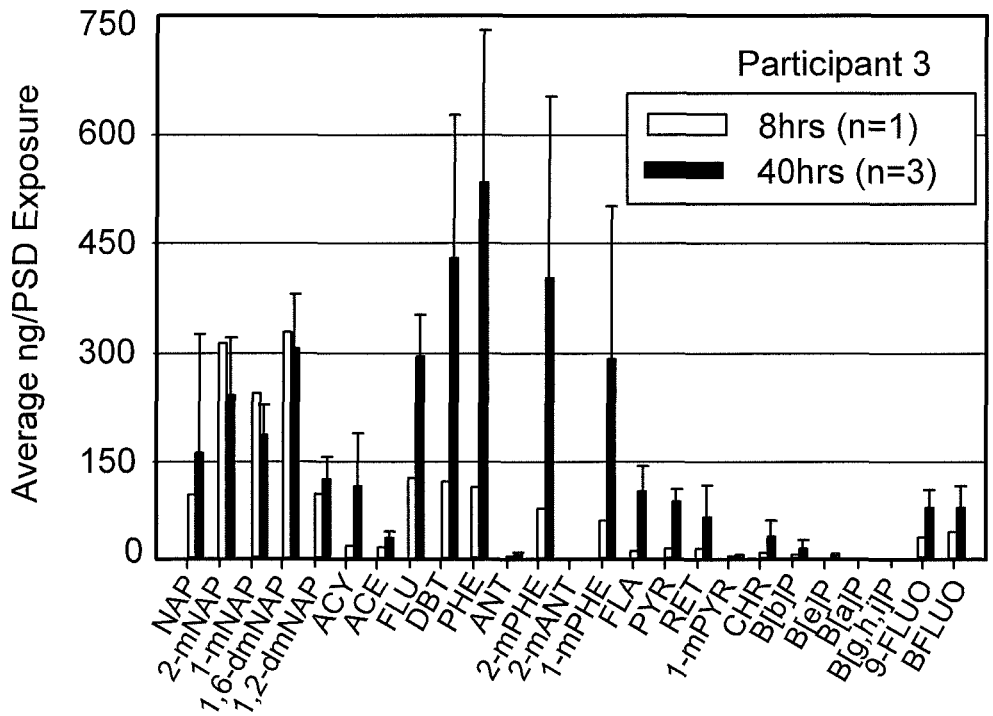

FIGS. 12B-12D show the amount of each of 23 PAH and OPAH compounds detected in the wristbands worn by three participants. Each bar represents an average across the three wristband configurations worn by the participant. The individual profiles of FIGS. 12A-12D are scaled equally to depict differences in detected compounds and overall profiles across participants. Phenanthrene and alkylated phenanthrenes were the most commonly detected and most abundant PAH compounds.

22 out of 23 PAH and OPAH compounds detected in the workweek deployment were also detected in the single day deployment, indicating that the wristband can effectively sequester compounds over a single day period. Benzo[e]pyrene was detected in the single day wristbands, demonstrating that large PAH compounds can be detected in a relatively short exposure period. Benzo[a]pyrene was not detected in the single day deployment. However, because benzo[a]pyrene was detected at just above the reporting limit in the workweek wristbands, it is likely that benzo[a]pyrene had also been sequestered by the single day wristbands, just at a concentration that was too low to detect.

Naphthalene and alkylated homologues were detected at a higher level in the single day wristbands than in the workweek wristbands. Differences in compound equilibrium between silicone and the atmosphere may explain this time profile of naphthalene in the wristbands. Napthalene is known to be difficult to interpret due to confounders such as cigarette smoking Participants 2 and 3 reported cigarette use; participant 1 did not.

The results discussed above can lead to casual observations about the spatial sensitivity of the wristbands. For instance, FIGS. 12A-12D demonstrate that the three participants at the rooftop worksite had generally similar profiles of PAH exposure, but the exposure magnitude differed between participant 1 and participants 2 and 3. Survey information indicated that participant 1 was a safety monitor at the worksite, while participants 2 and 3 were journeyman roofing professionals who directly handled the hot asphalt. Similarly, the results shown in FIGS. 9A and 9B demonstrate that a significant difference in PAH exposure exists between the rooftop worksite and the training site ($p<0.05$, power=0.99). In particular, the training site had a higher average PAH concentration than the rooftop worksite (training site 3040±1090 ng per wristband; rooftop worksite 800±570 ng per wristband). Survey information indicated that while hot asphalt was used at both sites, there were differences in the work enclosures. In particular, at the training site, hot asphalt was used to build a simulated roof at ground level in a semi-enclosed outdoor space. At the rooftop worksite, hot asphalt was used on the rooftop only after old roofing material had been removed, thus reducing some of the asphalt exposure. These observations indicate that silicone wristbands can be used for accurate exposure monitoring reflective of actual exposure conditions in real world situations.

The results of the analysis of the occupational deployment wristbands were analyzed using normality and equal variance tests. Once the normality and equal variance tests passed criteria, parametric t tests were performed with an assumed alpha value of 0.05. The power and p-value for the t-tests are referred to in the foregoing example. In this example, PAHs were not back-calculated to atmospheric concentration.

Example 6

Wristband Stability

Studies were carried out to examine whether PAHs would degrade after being sequestered by a wristband or whether field or handling conditions would influence exposure concentrations determined during wristband analysis. Wristbands were infused with several PAHs (fluorene-d10, benzo[b]fluoranthene-d12, fluorene, pyrene, and benzo[b]fluoranthene) and either exposed outdoors (in sun or shade) or placed in PTFE storage bags (at −20° C., 23° C., or 35° C.).

In particular, the wristbands exposed outdoors were placed on pre-rinsed foil and exposed for four hours either on an exposed aluminum 3 m rooftop (for direct sunlight) or underneath the roof between support beams (for shade). The exposures took place in September, 2013, between 11:30 am-3:30 pm, on a clear day in Corvallis, Oreg. The distance between each set of samples was less than 2 meters. The shade-exposed samples were protected from sunlight from above and below, but not from the sides, so that air flow can be assumed to be similar between the sunlight samples and the shade samples. Data loggers (Onset Computer Corp., Bourne, Mass.) were used to log changes in temperature throughout the exposure. The temperature difference between the sunlight samples and the shade samples was nearly 8° C. (shade: 22.6° C.; sun: 30.4° C.).

Figure 13:
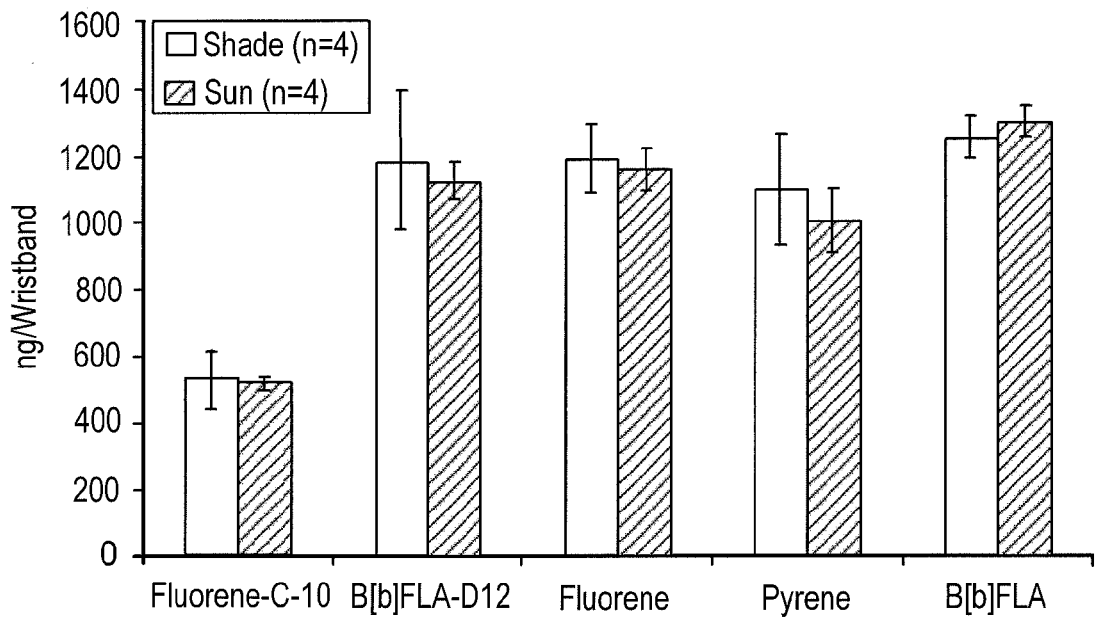
FIG. 13 is a plot of data from wristbands exposed to sun or shade.

Following sunlight or shade exposure, the PAHs were extracted from the wristbands using solvent extraction and analyzed as described above. Referring to FIG. 13, no significant differences in the amount of any of the PAHs was observed between the sunlight samples and the shade samples. The standard deviations in FIG. 13 are the result of four repeated experiments. These results are a preliminary indication that there is no photodegradation of compounds sequestered by the wristbands.

The PAH-infused wristbands placed in PTFE storage bags were exposed to a temperature of −20° C. (in a walk-in freezer), 23° C. (ambient temperature), or 35° C. (in a drying oven) for 72 hours. Temperatures in each environment were monitored every 30 minutes using a temperature logger. Following the 72-hour exposure, the PAHs were extracted from the wristbands using solvent extraction and analyzed as described above.

Figure 14:
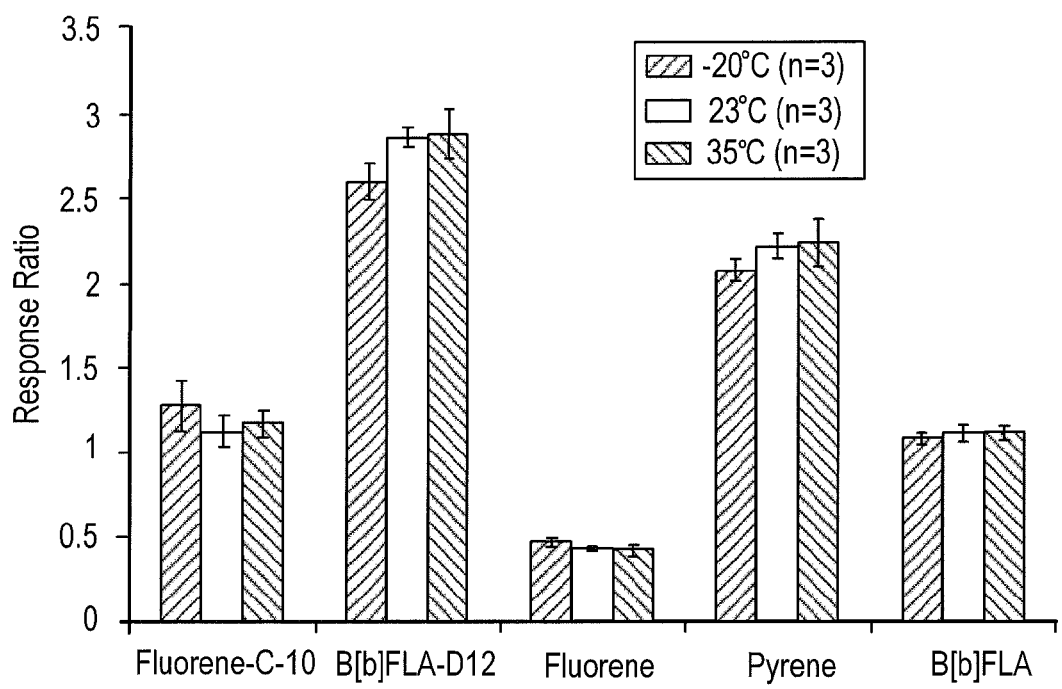
FIG. 14 is a plot of data from wristbands stored under various conditions over 3 days.

FIG. 14 shows the results of the analysis of the PTFE-stored wristbands. In FIG. 14, the ratio of each analyte response divided by an internal standard response (for perylene-d12) are shown, because an error with surrogate recovery artificially inflated the variance across the three temperature exposures. While fluorene appears to have significantly different response ratios across the three temperature exposures (one-way ANOVA, $p=0.03$), pairwise comparisons with the Holm-Sidak method does not report significant changes between any two temperature groups. The largest change among all PAH analytes was still less than 13% (fluorene-d10, freezer and ambient temperatures), so any changes in PAH concentrations were deemed negligible. Furthermore, potential changes in concentration would have been conserved since transportation was similar among wristbands within each temperature group. These data suggest that transportation of wristbands in PTFE bags with temperatures as high as 35° C. and with transport times as long as 72 hours does not affect the recovery of target analytes from the wristbands. The standard deviations in FIG. 14 are the result of three replicates.

In another example, the stability of wristbands infused with 17 compounds of varied physiochemistry was studied for various combinations of times and temperatures. Eighty wristbands were infused with the 17 compounds listed in Table 5. The compounds had $K_{ow}$ values ranging from 3.39 (anthraquinone-d8) to 13.265 (PDBE 154). Twelve wristbands underwent solvent extraction and analysis immediately following infusion. The remaining wristbands were divided into three groups and one group of wristbands was stored at each of −20° C., 4° C., and 30° C. Four wristbands from each temperature group underwent solvent extraction and analysis after 7 days and after 28 days. Four wristbands from the −20° C. and 4° C. temperature groups underwent solvent extraction and analysis after 14 days. This stability study is ongoing and will span 2 years.

Figure 15:
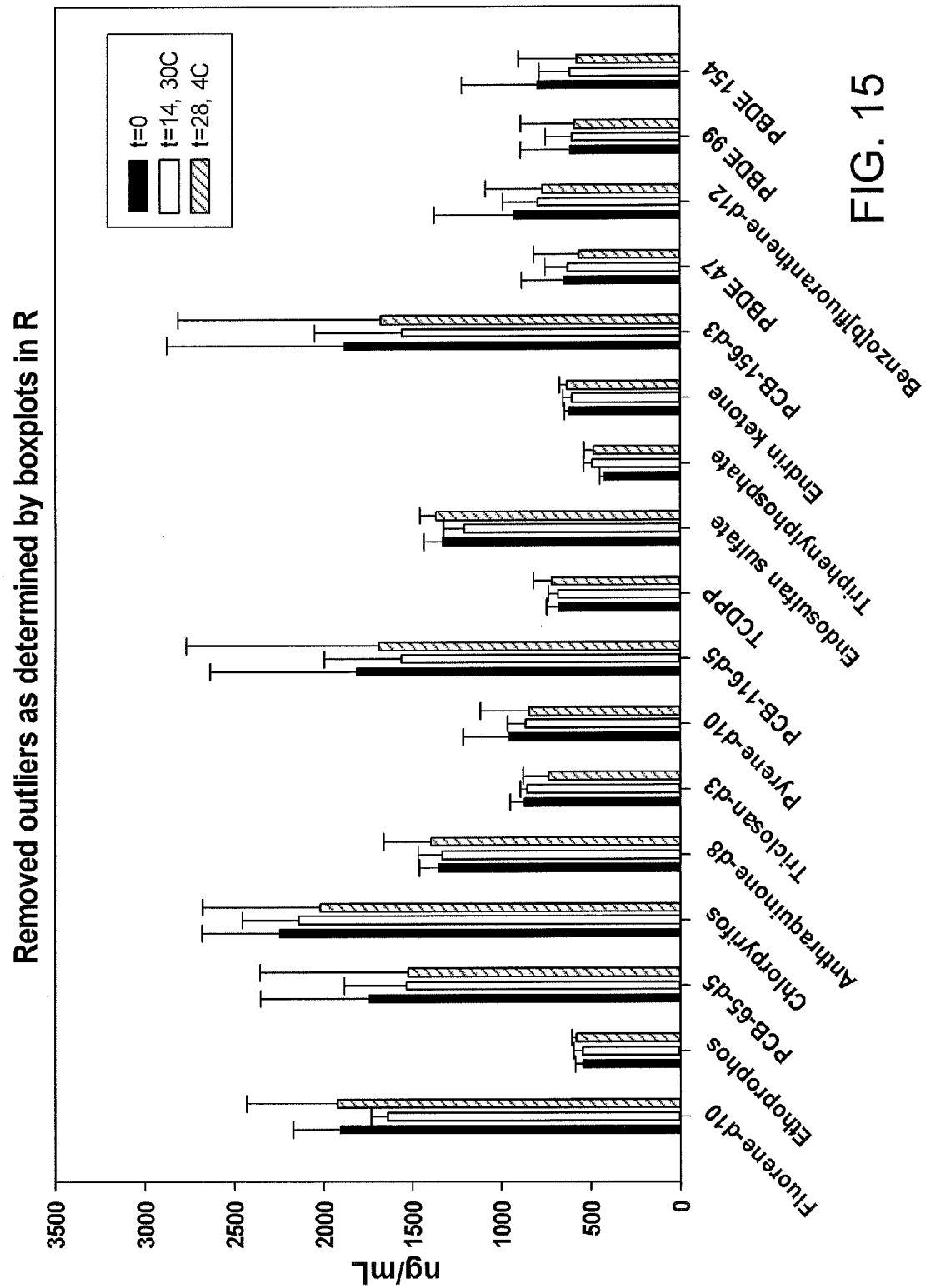
FIG. 15 is a plot of data from wristbands stored under various conditions over 0, 14, and 28 days.

Table 5 shows the relative standard deviation (RSD) of the concentration of each compound (in ng/mL) at the start of the study and the overall RSD across all time and temperature samples. A comparison between the initial RSD and the overall RSD for each compound reveals little difference in variability, indicating that the compounds are not changing significantly while sequestered in the wristband, despite being exposed to different storage times and temperatures. In addition, referring to FIG. 15, a bar graph of the average concentrations for each compound reveals no significant decrease in averages across all compounds. These results indicate that compounds are generally stable when sequestered in the wristbands.

TABLE 5

Stability of compounds in stored wristbands.

| | Compound | Beginning RSD from starting time point | Overall RSD from entire study to 28 days |
|---|---|---|---|
| 1 | endrin Ketone | 4% | 8% |
| 2 | endosulfan sulfate | 8% | 10% |
| 3 | triclosan-d3 | 9% | 11% |
| 4 | prophos/ethoprophos | 8% | 11% |
| 5 | Triphenylphosphate | 6% | 12% |
| 6 | TCDPP (1,3-dichloro-2-propyl phosphate) | 10% | 14% |
| 7 | Anthraquinone-d8 | 8% | 14% |
| 8 | fluorene-d10 | 14% | 16% |
| 9 | chlorpyrifos | 19% | 24% |
| 10 | pyrene-d10 | 27% | 32% |
| 11 | PBDE 47 | 37% | 37% |
| 12 | PCB-65-d5 | 35% | 37% |
| 13 | PBDE 99 | 46% | 43% |
| 14 | PCB-116-d5 | 45% | 44% |
| 15 | Benzo[b]fluoranthene-d12 | 49% | 45% |
| 16 | PCB-156-d3 | 53% | 50% |
| 17 | PBDE 154 | 53% | 51% |

Other implementations are also within the scope of the following claims.

What is claimed is:

1. A method comprising:
receiving a wearable monitoring device previously worn by a user and information indicative of an amount of time the wearable monitoring device was exposed to an environment, wherein when worn by the user, the wearable monitoring device comprises an absorbent material without a housing;
extracting one or more compounds from the wearable monitoring device;
analyzing the extracted compounds, wherein analyzing the extracted compounds comprises determining at least an amount of a reference compound extracted from the wearable monitoring device and an amount of an environmental compound extracted from the wearable monitoring device; and
based on the amount of the reference compound and the amount of the environmental compound and the information indicative of the amount of time, determining information indicative of the user's exposure to the environmental compound in the environment.

2. The method of claim 1, comprising purifying the wearable monitoring device; wherein the purified wearable monitoring device is provided to the user to be worn in the environment.

3. The method of claim 2, wherein purifying the wearable monitoring device comprises cleaning the wearable monitoring device with a solvent.

4. The method of claim 2, wherein purifying the wearable monitoring device comprises heat treating the wearable monitoring device.

5. The method of claim 2, comprising providing a purified wearable monitoring device to the user in an airtight container.

6. The method of claim 5, comprising receiving, from the user, the wearable monitoring device in the airtight container.

7. The method of claim 5, wherein the airtight container comprises a re-sealable bag.

8. The method of claim 1, comprising infusing a reference compound into the wearable monitoring device, wherein the infused wearable monitoring device is provided to the user to be worn in the environment.

9. The method of claim 1, comprising providing pre-paid return packaging to the user, and wherein receiving the wearable monitoring device from the user comprises receiving the wearable monitoring device in the pre-paid return packaging.

10. The method of claim 1, wherein extracting one or more compounds from the wearable monitoring device comprises extracting the compounds using a solvent extraction process.

11. The method of claim 10, comprising extracting the compounds into a solvent that is compatible with gas chromatography and liquid chromatography.

12. The method of claim 10, comprising extracting the compounds into ethyl acetate.

13. The method of claim 1, wherein extracting one or more compounds from the wearable monitoring device comprises thermally desorbing the compounds from the wearable monitoring device.

14. The method of claim 1, wherein extracting one or more compounds from the wearable monitoring device comprises extracting one or more of polycyclic aromatic hydrocarbon compounds, compounds from consumer products, pesticides, phthalates, industrial compounds, or volatile organic compounds.

15. The method of claim 1, in which analyzing the extracted compounds comprises determining one or more of an identity of each of the compounds or an amount of each of the compounds present in the wearable monitoring device.

16. The method of claim 1, in which determining information indicative of the user's exposure to the compounds in the environment comprises determining a time-weighted average of the user's exposure to each of the compounds.

17. The method of claim 1, comprising archiving one or more of (i) the extracted compounds or (ii) all or a portion of the wearable monitoring device.

18. The method of claim 1, wherein the wearable monitoring device comprises an article formed of silicone.

19. The method of claim 18, wherein extracting the one or more compounds from the wearable monitoring device comprises extracting the one or more compounds from the silicone.

20. The method of claim 18, wherein when the wearable monitoring device is received, the one or more compounds are sequestered in the silicone.

21. The method of claim 18, wherein the article formed of silicone is a personal accessory.

22. The method of claim 1, wherein the wearable monitoring device comprises a wristband.

23. A method comprising:
removing a purified wearable monitoring device from an airtight package;
exposing the wearable monitoring device to an environment, the exposing comprising attaching the wearable monitoring device to a user, wherein the wearable monitoring device that is exposed to the environment and attached to the user comprises an absorbent material without a housing;
tracking an amount of time for which the wearable monitoring device is exposed to the environment; and
sealing the wearable monitoring device in an airtight package for transport to an analysis facility for analysis of compounds sequestered by the wearable monitoring device during exposure of the wearable monitoring device to the environment.

24. The method of claim 23, wherein the wearable monitoring device comprises a wristband.

25. The method of claim 23, wherein exposing the wearable monitoring device to an environment comprises wearing the wearable monitoring device in the environment.

26. The method of claim 23, comprising intermittently exposing the wearable monitoring device to the environment; and tracking a total amount of time for which the wearable monitoring device is exposed to the environment.

27. The method of claim 23, comprising including, in or with the airtight package, an indication of the amount of time for which the wearable monitoring device was exposed to the environment.

28. A method comprising:
   receiving a wearable monitoring device previously worn by a user and information indicative of an amount of time the wearable monitoring device was exposed to an environment, wherein when worn by the user, the wearable monitoring device comprises an absorbent material without a housing;
   extracting one or more compounds from the absorbent material;
   analyzing the extracted compounds; and
   based on the analysis of the extracted compounds and the information indicative of the amount of time, determining information indicative of the user's exposure to the one or more compounds in the environment.

29. The method of claim 28, wherein the absorbent material comprises silicone.

30. The method of claim 28, wherein when the wearable monitoring device is received, the one or more compounds are sequestered in the absorbent material.

31. The method of claim 28, wherein the wearable monitoring device comprises a personal accessory formed of the absorbent material.

32. The method of claim 31, wherein the personal accessory comprises a wristband.

33. A method comprising:
   receiving a wearable monitoring device previously worn by a user and information indicative of an amount of time the wearable monitoring device was exposed to an environment, wherein when worn by the user, the wearable monitoring device comprises an absorbent material without a housing;
   cleaning an exterior surface of the absorbent material of the wearable monitoring device;
   extracting one or more compounds from the cleaned absorbent material of the wearable monitoring device;
   analyzing the extracted compounds; and
   based on the analysis of the extracted compounds and the information indicative of the amount of time, determining information indicative of the user's exposure to the one or more compounds in the environment.

34. The method of claim 33, wherein cleaning the exterior surface of the absorbent material comprises rinsing the absorbent material with water or an organic solvent.

35. The method of claim 33, wherein cleaning the exterior surface of the absorbent material comprises soaking the absorbent material in an acid.

36. The method of claim 33, wherein cleaning the exterior surface of the absorbent material comprises sonicating the absorbent material.

37. The method of claim 33, wherein the absorbent material comprises silicone.

38. The method of claim 37, wherein the wearable monitoring device comprises a personal accessory formed of silicone.

39. The method of claim 33, wherein when the wearable monitoring device is received, the one or more compounds are sequestered in the absorbent material.

* * * * *